US007682619B2

(12) United States Patent
Dubovi

(10) Patent No.: US 7,682,619 B2
(45) Date of Patent: Mar. 23, 2010

(54) CANINE INFLUENZA VIRUS

(75) Inventor: Edward J. Dubovi, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/697,285

(22) Filed: Apr. 5, 2007

(65) Prior Publication Data

US 2007/0253981 A1   Nov. 1, 2007

Related U.S. Application Data

(60) Provisional application No. 60/789,795, filed on Apr. 6, 2006.

(51) Int. Cl.
  A61K 39/38   (2006.01)
  A61K 39/00   (2006.01)
  A61K 39/12   (2006.01)
  A61K 39/145  (2006.01)
  C12P 21/04   (2006.01)
  C12N 5/02    (2006.01)
  A61K 39/205  (2006.01)

(52) U.S. Cl. .............. 424/209.1; 424/206.1; 424/205.1; 424/184.1; 424/185.1; 424/186.1; 435/70.1; 435/325

(58) Field of Classification Search ........................ None
See application file for complete search history.

(56) References Cited

U.S. PATENT DOCUMENTS

| 3,201,475 A | 8/1965 | Cavallini et al. |
| 3,518,347 A | 6/1970 | Pavilanis et al. |
| 3,773,928 A | 11/1973 | Huber et al. |
| 3,888,989 A | 6/1975 | Blaszczak |
| 3,904,750 A | 9/1975 | Lief |
| 3,950,512 A | 4/1976 | Emery et al. |
| 4,112,068 A | 9/1978 | Cabasso |
| 4,429,045 A | 1/1984 | Bass et al. |
| 4,466,957 A | 8/1984 | Hjorth et al. |
| 4,567,042 A | 1/1986 | Acree et al. |
| 4,567,043 A | 1/1986 | Acree et al. |
| 4,584,194 A | 4/1986 | Bass et al. |
| 4,689,224 A | 8/1987 | Bull et al. |
| 4,711,778 A | 12/1987 | Bass et al. |
| 4,716,030 A | 12/1987 | Macy |
| 4,726,946 A | 2/1988 | Bass et al. |
| 4,810,494 A | 3/1989 | Welsh |
| 4,824,785 A | 4/1989 | Acree et al. |
| 4,888,169 A | 12/1989 | Brown et al. |
| 4,920,213 A | 4/1990 | Dale et al. |
| 5,000,951 A | 3/1991 | Bass et al. |
| 5,013,663 A | 5/1991 | Acree et al. |
| 5,019,388 A | 5/1991 | Brown et al. |
| 5,047,238 A | 9/1991 | Acree et al. |
| 5,200,179 A | 4/1993 | Bordt et al. |
| 5,316,764 A | 5/1994 | Walsh |
| 5,484,719 A | 1/1996 | Lam et al. |
| 5,651,972 A | 7/1997 | Moyer et al. |
| 5,661,006 A | 8/1997 | Brown et al. |
| 5,690,942 A | 11/1997 | Hjorth |
| 5,718,904 A | 2/1998 | Hjorth |
| 5,750,112 A | 5/1998 | Gill |
| 6,165,481 A | 12/2000 | Kaiya et al. |
| 6,217,882 B1 | 4/2001 | Moyer et al. |
| 6,287,254 B1 | 9/2001 | Dodds |
| 6,309,647 B1 | 10/2001 | Paoletti et al. |
| 6,310,090 B1 | 10/2001 | Hayek |
| 6,348,568 B1 | 2/2002 | Barney et al. |
| 6,368,603 B1 | 4/2002 | Jarecki-Black |
| 6,537,213 B2 | 3/2003 | Dodds |
| 6,723,324 B2 | 4/2004 | Schrier et al. |
| 6,841,555 B2 | 1/2005 | Behforouz et al. |
| 6,927,062 B2 | 8/2005 | Schoedel |
| 7,029,441 B2 | 4/2006 | Dodds |
| 7,468,187 B2 | 12/2008 | Yoon et al. |
| 2001/0006673 A1 | 7/2001 | Hayek |
| 2002/0022772 A1 | 2/2002 | Dodds |
| 2002/0058039 A1 | 5/2002 | Coyne et al. |
| 2002/0081655 A1 | 6/2002 | Savitzky et al. |
| 2003/0013942 A1 | 1/2003 | Dodds |
| 2003/0129161 A1 | 7/2003 | Chu |
| 2003/0139655 A1 | 7/2003 | Dodds |
| 2003/0180328 A1 | 9/2003 | Bogoch et al. |
| 2003/0190314 A1 | 10/2003 | Campbell et al. |
| 2003/0194414 A1 | 10/2003 | Bogoch et al. |
| 2003/0219460 A1 | 11/2003 | David et al. |
| 2004/0019053 A1 | 1/2004 | Roark |
| 2004/0019054 A1 | 1/2004 | Roark |
| 2004/0039258 A1 | 2/2004 | Jean |
| 2004/0043983 A1 | 3/2004 | Li |
| 2004/0043985 A1 | 3/2004 | Hicks et al. |
| 2004/0086527 A1 | 5/2004 | Schlegel et al. |

(Continued)

FOREIGN PATENT DOCUMENTS

BE   859178 A   1/1978

(Continued)

OTHER PUBLICATIONS

Veterinary Advisory, Aug. 12, 2005, Canine Influenza Virus (Canine Flu) Downloaded from http://www.vetmed.ufl.edu/pr/nw_story/CANINEFLUFACTSHEET.htm on Jan. 10, 2008.*

(Continued)

Primary Examiner—Gary B Nickol
Assistant Examiner—Benjamin P Blumel
(74) Attorney, Agent, or Firm—Nixon Peabody LLP

(57) ABSTRACT

The present invention relates to an isolate canine influenza virus. The present invention relates to an isolated nucleic acid molecule encoding a hemagglutinin from a canine influenza virus. The present invention also relates to the protein or polypeptide encoded by the isolated nucleic acid molecule. Vaccines and detection and treatment methods relating to canine influenza viruses are also disclosed.

17 Claims, 3 Drawing Sheets

U.S. PATENT DOCUMENTS

| | | |
|---|---|---|
| 2004/0101972 A1 | 5/2004 | Schoedel |
| 2004/0142398 A1 | 7/2004 | Bandla et al. |
| 2004/0151761 A1 | 8/2004 | Chew et al. |
| 2004/0248922 A1 | 12/2004 | Behforouz et al. |
| 2005/0032034 A1 | 2/2005 | Dodds |
| 2005/0032732 A1 | 2/2005 | Lai |
| 2005/0089533 A1 | 4/2005 | Frantz et al. |
| 2005/0090718 A1 | 4/2005 | Dodds |
| 2005/0152884 A1 | 7/2005 | Boileau et al. |
| 2005/0158293 A1 | 7/2005 | Boileau et al. |
| 2005/0158294 A1 | 7/2005 | Boileau et al. |
| 2005/0175598 A1 | 8/2005 | Boileau et al. |
| 2005/0260618 A1 | 11/2005 | Cullor et al. |
| 2006/0014140 A1 | 1/2006 | Boivin |
| 2006/0116721 A1 | 6/2006 | Yun et al. |
| 2006/0153871 A1 | 7/2006 | Olsen et al. |
| 2006/0205059 A1 | 9/2006 | Esfandiari |
| 2006/0228448 A1 | 10/2006 | Boileau et al. |
| 2006/0251674 A1 | 11/2006 | Dominowski et al. |
| 2006/0252049 A1 | 11/2006 | Shuler et al. |
| 2007/0031450 A1 | 2/2007 | Kumar et al. |
| 2007/0031941 A1 | 2/2007 | Duke et al. |
| 2007/0042001 A1 | 2/2007 | Weeks-Levy et al. |
| 2007/0042002 A1 | 2/2007 | Weeks-Levy et al. |
| 2007/0048821 A1 | 3/2007 | Minke et al. |
| 2007/0082012 A1 | 4/2007 | Shields et al. |

FOREIGN PATENT DOCUMENTS

| | | |
|---|---|---|
| CN | 1137347 A | 12/1996 |
| CN | 1547027 A | 11/2004 |
| CN | 1648134 A | 8/2005 |
| CN | 1654072 A | 8/2005 |
| CN | 1861634 A | 11/2006 |
| CN | 1876181 A | 12/2006 |
| CN | 1887344 A | 1/2007 |
| DE | 1124963 A | 0/1968 |
| DE | 2405675 A | 8/1974 |
| EP | 0 044 920 A2 | 2/1982 |
| EP | 0 189 958 A2 | 8/1986 |
| EP | 0 310 316 A2 | 4/1989 |
| EP | 0 465 204 B1 | 1/1992 |
| EP | 1 016 416 A2 | 7/2000 |
| EP | 1 067 179 A1 | 1/2001 |
| EP | 1 156 333 A1 | 11/2001 |
| EP | 1 238 983 A1 | 9/2002 |
| EP | 0 947 491 B1 | 5/2004 |
| FR | 2751226 A1 | 1/1998 |
| FR | 2776928 A1 | 10/1999 |
| GB | 886965 | 1/1962 |
| JP | 47011597 A | 0/1972 |
| JP | 57056430 A | 4/1982 |
| JP | 58116422 A | 7/1983 |
| JP | 06228010 A | 8/1994 |
| JP | 2004-258814 | 9/2004 |
| JP | 2006008594 A | 1/2006 |
| JP | 2006-265197 A | 10/2006 |
| KR | 2002068923 A | 8/2002 |
| KR | 2004046594 A | 6/2004 |
| SU | 1703121 A1 | 1/1992 |
| WO | WO 85/00014 A1 | 1/1985 |
| WO | WO 86/07593 A1 | 12/1986 |
| WO | WO 91/02054 A1 | 2/1991 |
| WO | WO 92/15672 A1 | 9/1992 |
| WO | WO 94/09035 A1 | 4/1994 |
| WO | WO 95/22314 A1 | 8/1995 |
| WO | WO 95/24214 A1 | 9/1995 |
| WO | WO 96/15232 A1 | 5/1996 |
| WO | WO 96/40241 A1 | 12/1996 |
| WO | WO 96/40869 A1 | 12/1996 |
| WO | WO 97/07133 A1 | 2/1997 |
| WO | WO 97/34008 A1 | 9/1997 |
| WO | WO 97/49825 A1 | 12/1997 |
| WO | WO 98/00166 A1 | 1/1998 |
| WO | WO 98/07443 A1 | 2/1998 |
| WO | WO 98/52603 A2 | 11/1998 |
| WO | WO 98/56366 A1 | 12/1998 |
| WO | WO 99/00147 A1 | 1/1999 |
| WO | WO 99/29872 A1 | 6/1999 |
| WO | WO 99/40438 A1 | 8/1999 |
| WO | WO 99/44633 A1 | 9/1999 |
| WO | WO 99/59630 A1 | 11/1999 |
| WO | WO 00/09702 A1 | 2/2000 |
| WO | WO 00/77043 A2 | 12/2000 |
| WO | WO 01/03723 A1 | 1/2001 |
| WO | WO 01/28584 A1 | 4/2001 |
| WO | WO 01/51673 A2 | 7/2001 |
| WO | WO 01/60849 A2 | 8/2001 |
| WO | WO 01/64013 A2 | 9/2001 |
| WO | WO 01/70032 A1 | 9/2001 |
| WO | WO 02/00883 A2 | 1/2002 |
| WO | WO 02/00885 A2 | 1/2002 |
| WO | WO 02/02139 A2 | 1/2002 |
| WO | WO 02/077211 A2 | 10/2002 |
| WO | WO 02/081655 A2 | 10/2002 |
| WO | WO 03/029912 A2 | 4/2003 |
| WO | WO 03/072720 A2 | 9/2003 |
| WO | WO 2004/011651 A1 | 2/2004 |
| WO | WO 2004/067031 A1 | 8/2004 |
| WO | WO 2004/080403 A2 | 9/2004 |
| WO | WO 2004/084941 A1 | 10/2004 |
| WO | WO 2005/002618 A1 | 1/2005 |
| WO | WO 2005/010032 A2 | 2/2005 |
| WO | WO 2005/012343 A1 | 2/2005 |
| WO | WO 2005/044992 A2 | 5/2005 |
| WO | WO 2005/060707 A2 | 7/2005 |
| WO | WO 2005/060709 A2 | 7/2005 |
| WO | WO 2005/062820 A2 | 7/2005 |
| WO | WO 2005/077299 A1 | 8/2005 |
| WO | WO 2005/097165 A2 | 10/2005 |
| WO | WO 2005/112993 A1 | 12/2005 |
| WO | WO 2005/115448 A2 | 12/2005 |
| WO | WO 2006/044694 A2 | 4/2006 |
| WO | WO 2006/051069 A2 | 5/2006 |
| WO | WO 2006/067211 A1 | 6/2006 |
| WO | WO 2006/088962 A2 | 8/2006 |
| WO | WO 2006/095431 A1 | 9/2006 |
| WO | WO 2006/098804 A2 | 9/2006 |
| WO | WO 2006/106424 A2 | 10/2006 |
| WO | WO 2006/110406 A2 | 10/2006 |
| WO | WO 2006/116082 A1 | 11/2006 |
| WO | WO2006/116082 A1 | 11/2006 |
| WO | WO 2007/002008 A2 | 1/2007 |
| WO | WO 2007/008605 A1 | 1/2007 |
| WO | WO 2007/024947 A2 | 3/2007 |
| WO | WO 2007/035455 A2 | 3/2007 |
| WO | WO 2007/047728 A2 | 4/2007 |
| WO | WO 2007/047938 A2 | 4/2007 |
| WO | WO 2007/048086 A2 | 4/2007 |
| WO | WO 2007/048089 A2 | 4/2007 |
| ZA | 66/6723 A | 11/1965 |

OTHER PUBLICATIONS

Canine Influenza Backgrounder, Feb. 14, 2007 American Veterinary Medical Association, Dowloaded from http://www.avma.org/public_health/influenza/canine_bgnd.asp on Jan. 10, 2008.*

Crawford et al., Transmission of Equine Influenza Virus to Dogs, 2005, Science, vol. 310, pp. 482-485.*

Genbank Accession # ABA41538, Hemagglutinin protein [Influenza A virus (A/canine/Iowa/13628/2005 (H3N8))], published on Nov. 16, 2005.*

Genbank Accession # DQ146419, Hemagglutinin gene [Influenza A virus (A/canine/Iowa/13628/2005 (H3N8))], published on Nov. 16, 2005.*

Abdelmagid et al., "Evaluation of the Efficacy and Duration of Immunity of a Canine Combination Vaccine Against Virulent Parvovirus, Infectious Canine Hepatitis Virus, and Distemper Virus Experimental Challenges," *Vet. Ther.* 5(3):173-86 (2004).

Acree et al., "Serological and Safety Evaluation of a Combination Distemper-Hepatitis-Parainfluenza-Parvovirus Vaccine with Leptospira Bacterin in Dogs," *Canine Pract.* 9(5):19-21 (1982).

Adeyefa et al., "Mutational Changes in the Hemagglutinin of Equine H3 Influenza Viruses Result in the Introduction of a Glycosylation Site Which Enhances the Infectivity of the Viruses," *Folia Microbiol.* 42(4):390-394 (1997).

Alkire & Chladek, "Field Evaluation of an Intranasally Administered Canine Parainfluenza-*Bordetella bronchiseptica* Vaccine," *Vet. Med.* 75(6):1003-5 (1980).

Anon., "Canine Influenza Virus Test," *J. Am. Assoc. Lab. Anim. Sci.* 45(1):136 (2006).

Appel & Paoletti, "Immune Response to Vaccinia Virus and Recombinant Virus Products in Dogs," *Am. J. Vet. Res.* 49(11):1932-4 (1988).

Aubert et al., "Protection Conférée par un Vaccin Canin Multivalent Canigen$^R$ CH$_{A2}$PPI/Lr vis-à-vis du Complexe Infectieux <<Toux des Chenils>> [Protection Conferred by a Multivalent Vaccine Canigen$^R$ CH$_{A2}$PPI/LR Against Kennel Cough]," *Rev. Med. Vet.* 142(2):131-138, at Abstract (1991).

Bass et al., "Development of a Modified Live, Canine Origin Parvovirus Vaccine," *J. Am. Vet. Med. Assoc.* 181(9):909-13 (1982).

Bass et al., "Evaluation of a Canine Adenovirus Type 2 Strain as a Replacement for Infectious Canine Hepatitis Vaccine," *J. Am. Vet. Med. Assoc.* 177(3):234-242 (1980).

Baty et al., "Sequence Comparison Between the Hemagglutinin—neuraminidase Genes of Simian, Canine and Human Isolates of Simian Virus 5," *J. Gen. Virol.* 72(12):3103-7 (1991).

Bean et al., "Evolution of the H3 Influenza Virus Hemagglutinin from Human and Nonhuman Hosts," *J. Virol.* 66(2):1129-38 (1992).

Benary F., *Untersuchungen uber die Antikorperbildung bei Hunden nach der Impfung mit einer Reo-infuenza A2/Hong Kong—Kombinationvaccine* [*Studies in Antibody Formation in Dogs after Vaccination with a Reovirus-influenza A2/Hong Kong Combined Vaccine*] 1-112, at Abstract (Dissertation 1975).

Bibrack & Benary, "Seroepizootologische Untersuchungen über die Bedeutung von Parainfluenza-2-infektionen beim Zwingerhusten in Deutschland [Seroepizootologic Studies on the Importance of Parainfluenza 2 Infection in Kennel Cough in Germany]," *Zbl. Vet. Med. B* 22(7):610-614, at Summary (1975).

Binn et al., "Studies of Respiratory Disease in Random-source Laboratory Dogs: Viral Infections in Unconditioned Dogs," *Lab. Anim. Sci.* 29(1):48-52 (1979).

Binn et al., "Viral Antibody Patterns in Laboratory Dogs with Respiratory Disease," *Am. J. Vet. Res.* 31(4):697-702 (1970).

Binn et al., "Viral Antibody Studies of Laboratory Dogs with Diarrheal Disease," *Am. J. Vet. Res.* 42(10):1665-7 (1981).

Binns et al., "Genetic and Antigenic Analysis of an Equine Influenza H3 Isolate from the 1989 Epidemic," *Arch. Virol.* 130:33-43; 133(1-2):235-7 (errata) (1993).

Bonde et al., "Seroprevalence of *Bordetella bronchiseptica* and *Canine Parainfluenza* Virus Type 2 in Dogs in Bombay," *J. Bombay Vet. Coll.* 2(2):79-82 (1990).

Brands et al., "Influvac$^{Tc}$: A Safe Madin Darby Canine Kidney (MDCK) Cell Culture-based Influenza Vaccine," *Dev. Biol. Stand.* 98:93-100 (1999).

Breiteneder-Geleff et al., "Podoplanin, Novel 43-kd Membrane Protein of Glomerular Epithelial Cells, Is Down-regulated in Puromycin Nephrosis," *Am. J. Pathol.* 151(4):1141-1152 (1997).

Brown et al., "An Alternative Method for Evaluating Potency of Modified Live Canine Parainfluenza Virus Vaccine," *J. Biol. Stand.* 6(4):271-81 (1978).

Browne, "Mechanism and Specificity of Action of Ribavirin," *Antimicrob. Agents Chemother.* 15(6):747-753 (1978).

Buonavoglia & Martella, "Canine Respiratory Viruses," *Vet. Res.* 38(2):355-373 (2007).

Buonavoglia & Sala, "Indagine Sierologica in Cani Sulla Presenza di Anticorpi Verso Ceppi di Virus Influenzali Umani Tipo A [Serological Survey for Antibody to Human Influenza A Viruses Strains in Dogs]," *Clinica Veterinaria* 106(5):81-83, at Summary (1983).

Cascino et al., "A Nonneutralizing Human IgM Monoclonal Antibody Inhibiting Hemagglutination of H3N2 Influenza A Strains," *Hybridoma* 5(4):307-18 (1986).

Chladek et al., "Canine Parainfluenza-*Bordetella bronchiseptica* Vaccine: Immunogenicity," *Am. J. Vet. Res.* 42(2):266-70 (1981).

Chrobocińska & Górski, "Wystepowanie Przeciwcial Przeciw Wirusowi Parainfluenzy Typ 2 i Adenowirusowi Typ 2 w Surowicach Psów [Prevalence of Antibodies Against Parainfluenza Virus Type 2 and Adenovirus Type 2 in Canine Sera of Dogs]," *Medycyna Wet.* 51(4):203-205, at Summary (1995).

Colzani et al, "Efficacia della Vaccinazione Contro la Parainfluenza del Cane e Sua Interferenza verso Altre Profilassi Vaccinali [Efficacy of Vaccination Against Parainfluenza in Dogs and Its Compatibility with Other Vaccinations]," *Bollettino Associazione Italiana Veterinari per Piccoli Animali* 26(3):173-179, at Abstract (1987).

Cook & Cook, "Differences in Sensitivity in Haemagglutinin Inhibition Assays Between A/Equine/H3N8 Viruses Isolated in Eggs and MDCK Cells Are Linked to Cleavage of the Haemagglutinin Molecule," *Vet. Microbiol.* 27(3-4):253-261 (1991).

Crawford et al., "Crossreactivity of Canine and Equine Influenza Antibodies," *J. Vet. Int. Med.* 20(3):711, Abstract No. 7 (2006).

Crawford et al., "Response," *Science* 311(5765):1241-1242 (2006).

Crawford et al., "Supporting Online Material for Transmission of Equine Influenza Virus to Dogs," *Science*, www.sciencemag.org/cgi/content/ful/1117950/DC1 (Sep. 29, 2005).

Crawford et al., "Transmission of Equine Influenza Virus to Dogs," *Science* 310(5747):482-485 (2005).

Cvetnić & Čač, "Serološka Reakcija Različitih Životinja na Vakcinu Influence Konja [Serological Response of Various Animals to Equine Influenza Vaccine]," *Veterinarski Arhiv* 48(5):257-263, at Summary (1978).

Damián et al., "Immunohistochemical Detection of Antigens of Distemper, Adenovirus and Parainfluenza Viruses in Domestic Dogs with Pneumonia," *J. Comp. Pathol.* 133(4):289-293 (2005).

Daniels et al., "Amino Acid Sequences of Haemagglutinins of Influenza Viruses of the H$_3$ Subtype Isolated from Horses," *J. Gen. Virol.* 66(3):457-64 (1985).

Davidson et al., "Diseases and Parasites of Red Foxes, Gray Foxes, and Coyotes from Commercial Sources Selling to Fox-chasing Enclosures," *J. Wildlife Dis.* 28(4):581-9 (1992).

de Morais, "Influenza em Cães e Gatos [Influenza in Dogs and Cats]," *Clinica Veterinaria* 11(63):60-66, at Abstract (2006) V.

DePalma, "Cell Culture-based Vaccine Manufacturing," *Gen. Engin. News* 25(10):44-46 (2005).

Dhar et al., "Nonviral Oligonucleotides at the 5' Terminus of Cytoplasmic Influenza Viral MRNA Deduced from Cloned Complete Genomic Sequences," *Cell* 21(2):495-500 (1980).

Dinopoulos, *Contribution a l'Etude de la Toux de Chenil. Immunite vis a vis du Virus Parainfluenza Canin. Problemes Poses par la Protection des Chiots en Milieu Contamine* [*Kennel Cough: Immunity to Canine Parainfluenza Virus and Problems of Protecting Pups in a Contaminated Environment*] 1-70 (Dissertation 1985).

Doxsey et al., "An Efficient Method for Introducing Macromolecules into Living Cells," *J.Cell Biol.* 101(1):19-27 (1985).

Duval & Giger, "Vaccine-Associated Immune-Mediated Hemolytic Anemia in the Dog," *J. Vet. Int. Med.* 10(5):290-5 (1996).

Edinboro et al., "A Placebo-controlled Trial of Two Intranasal Vaccines to Prevent Tracheobronchitis (Kennel Cough) in Dogs Entering a Humane Shelter," *Prev. Vet. Med.* 62(2):89-99 (2004).

Edinboro et al., "Corrigendum to 'A Placebo-controlled trial of two Intranasal Vaccines to Prevent Tracheobronchitis (Kennel Cough) in Dogs Entering a Humane Shelter' [*Prev. Vet. Med.* 62 (2004) 89-99]," *Prev. Vet. Med.* 69(3-4):309-10 (2005).

Emery & Sweeny, "A Canine Parainfluenza Virus Vaccine," *Canine Pract.* 2(2):26-29 (1975).

Emery et al., "A Canine Parainfluenza Viral Vaccine: Immunogenicity and Safety," *Am. J. Vet. Res.* 37(11):1323-7 (1976).

Endo et al., "Evolutionary Pattern of the H3 Haemagglutinin of Equine Influenza Viruses: Multiple Evolutionary Lineages and Frozen Replication," *Arch. Virol.* 123(1-2):73-87 (1992).

Englund et al., "Seroepidemiological Survey of *Bordetella bronchiseptica* and Canine Parainfluenza-2 Virus in Dogs in Sweden," *Vet. Record* 152(9):251-4 (2003).

Erles & Brownlie, "Investigation into the Causes of Canine Infectious Respiratory Disease: Antibody Responses to Canine Respiratory Coronavirus and Canine Herpesvirus in Two Kennelled Dog Populations," *Arch. Virol.* 150(8):1493-1504 (2005).

Evermann et al., "Canine Fatalities Associated with the Use of a Modified Live Vaccine Administered During Late Stages of Pregnancy," *J. Vet. Diagn. Invest.* 6(3):353-357 (1994).

Fulton et al., "Serum Antibodies Against Canine Respiratory Viruses: Prevalence Among Dogs of Eastern Washington," *Am. J. Vet. Res.* 35(6):853-855 (1974).

Gaedke et al., "Nachweis von Staupevirus-N-protein-RNS im Gehirn von Hunden mit Spontaner Staupeenzephalitis mittels einer Digoxigenin-markierten, Doppelstrangigen DNS-sonde in der in Situ Hybridisierung [Detection of CDV-N-protein-RNA in the Brain of Dogs with Spontaneous Distemper Encephalitis with a Digoxigenin-labeled Double-stranded DNA-probe by in Situ Hybridization," *Berl. Münch. Tierärztl. Wschr.* 108(2):51-4, at Abstract (1995).

Gamoh et al., "Standardization of Methods of Determination of Content of Canine Parainfluenza Virus," *Ann. Rep. Nat'l. Vet. Assay Lab.* 31:9-13 at Abstract (1994).

Gao et al., "Construction and Experimental Immunity of Recombinant Replication-competent Canine Adenovirus Type 2 Expressing Hemagglutinin Gene of H5N1 Subtype Tiger Influenza Virus," *Acta Microbiol. Sinica* 46(2):297-300 at Abstract (2006).
Generalov et al., "Study of Virus-Cell Interaction by the Method of Dielectrophoresis," *Doklady Biochem. Biophy.* 383:82-84 (2002).
Glickman & Appel, "Intranasal Vaccine Trial for Canine Infectious Tracheobronchitis (Kennel Cough)," *Lab. Anim. Sci.* 31(4):397-9 (1981).
Halperin et al., "Safety and Immunogenicity of a New Influenza Vaccine Grown in Mammalian Cell Culture," *Vaccine* 16(13):1331-5 (1998).
Hampton, "Equine Influenza Jumps to Canines," *J. Am. Med. Assoc.* 294(16):2015 (2005).
Handt et al., "Clinical and Microbiologic Characterization of Hemorrhagic Pneumonia Due to Extraintestinal Pathogenic *Escherichia coli* in Four Young Dogs," *Compar. Med.* 53(6):663-670 (2003).
Harmon et al., "Antibody Response in Humans to Influenza Virus Type B Host-cell-derived Variants After Vaccination with Standard (Egg-derived) Vaccine or Natural Infection," *J. Clin. Microbiol.* 26(2):333-7 (1988).
Harrus et al., "Development of Hypertrophic Osteodystrophy and Antibody Response in a Litter of Vaccinated Weimaraner Puppies," *J. Small Anim. Prac.* 43(1):27-31 (2002).
Hebert et al., "Calnexin and Calreticulin Promote Folding, Delay Oligomerization and Suppress Degradation of Influenza Hemagglutinin in Microsomes," *EMBO J.* 15(12):2961-2968 (1996).
Hebert et al., "Glucose Trimming and Reglucosylation Determine Glycoprotein Association with Calnexin in the Endoplasmic Reticulum," *Cell* 81(3):425-33 (1995).
Holzman et al., "Diseases, Parasites and Survival of Coyotes in South-Central Georgia," *J. Wildlife Dis.* 28(4):572-80 (1992).
Houser & Heuschele, "Evidence of Prior Infection with Influenza A/Texas/77 ($H_3N_2$) Virus in Dogs with Clinical Parainfluenza," *Can. J. Compar. Med.* 44(4):396-402 (1980).
Ilobi et al., "Direct Sequencing of the HA Gene of Clinical Equine H3N8 Influenza Virus and Comparison with Laboratory Derived Viruses," *Arch. Virol.* 143(5):891-901 (1998).
Inoue et al., "Changes in Bronchial Reactivity to Acetylcholine with Type C Influenza Virus Infection in Dogs," *Am. Rev. Respir. Dis.* 133(3):367-71 (1986).
International Preliminary Report on Patentability for PCT Patent Application No. PCT/US2007/066169 (Oct. 8, 2008).
International Search Report for PCT Patent Application No. PCT/US2007/066169 (Jul. 31, 2008).
Istomina et al., "Comparative Virucidal Activity of Several New Disinfectants," Osnovn. Napravleniya Razvit. Nauki Prakt. Dezinfekts. Dela 18-20 at Abstract (1981).
Jacobs et al., "Compatibility of a Bivalent Modified-Live Vaccine Against *Bordetella bronchiseptica* and CPiV, and a Trivalent Modified-Live Vaccine Against CPV, CDV and CAV-2," *Vet. Record* 160(2):41-5 (2007).
Jacobs et al., "Protection of Dogs for 13 Months Against *Bordetella bronchiseptica* and Canine Parainfluenza Virus with a Modified Live Vaccine," *Vet. Record* 157(1):19-23 (2005).
Jin et al., "[Isolation and Identification of Canine Parainfluenza Attenuated Vaccine Strain]," at Abstract 21(6):722-724 Disi Junyi Daxue Xuebao [J. 4$^{th}$ Mil. Med. Univ.] (2000).
Jin et al., "[Isolation and Identification of Wild-type Strain of Canine Parainfluenza Virus]," at Abstract 21(6):719-721 (2000).
Johnson & Castro, "Isolation of Canine Parvovirus from a Dog Brain with Severe Necrotizing Vasculitis and Encephalomalacia," *J. Am. Vet. Med. Assoc.* 184(11):1398- 1399 (1984).
Karaca et al., "Evaluation of the Ability of Canarypox-vectored Equine Influenza Virus Vaccines to Induce Humoral Immune Responses Against Canine Influenza Viruses in Dogs," *Am. J. Vet. Res.* 68(2):208-12 (2007).
Kawano et al., "Complete Nucleotide Sequence of the Matrix Gene of Human Parainfluenza Type 2 Virus and Expression of the M Protein in Bacteria," *Virology* 179(2):857-861 (1990).
Kawaoka et al., "Evolution of the Hemagglutinin of Equine H3 Influenza Viruses," *Virology* 169(2):283-92 (1989).
Kilbourne & Kehoe, "Demonstration of Antibodies to Both Hemagglutinin and Neuraminidase Antigens of H3N2 Influenza A Virus in Domestic Dogs," *Intervirology* 6(4-5):315-318 (1975-1976).
Kilbourne, "Genetic Dimorphism in Influenza Viruses: Characterization of Stably Associated Hemagglutinin Mutants Differing in Antigenicity and Biological Properties," *Proc. Nat. Acad. Sci. USA* 75(12):6258-6262 (1978).
Kim et al., "[Studies on Development of Canine Parainfluenza Live Vaccine]," *Res. Rept. Rural Dev. Admin.* 32(3):48-56 at Abstract (1990).
Kim et al., "[Survey on Some Important Canine Infectious Diseases of Korean Jindo Dogs]," *Res. Rept. Rural Dev. Admin.* 33(2):61-68, at Abstract (1991).
Kimber et al., "Serologic Survey of Selected Viral Agents in Recently Captured Wild North American River Otters (*Lontra canadensis*)," *J. Zoo Wildlife Med.* 31(2):168-75 (2000).
Kishimoto et al., "Effects of Immunoglobulin Upon Murine Myocarditis Caused by Influenza A Virus: Superiority of Intact Type to F(ab')2 Type," *J. Cardiovasc. Pharmacol.* 43(1):61-67 (2004).
Kontor et al., "Canine Infectious Tracheobronchitis: Effects of an Intranasal Live Canine Parainfluenza-*Bordetella bronchiseptica* Vaccine on Viral Shedding and Clinical Tracheobronchitis (Kennel Cough)," *Am. J. Vet. Res.* 42(10):1694-8 (1981).
Krakowka et al, "Canine Parvovirus Infection Potentiates Canine Distemper Encephalitis Attributable to Modified Live-Virus Vaccine," *J. Am. Vet. Med. Assoc.* 180(2):137-9 (1982).
Kromeier, *Nicotin Beeinfluβt die Durch Influenza-A-Virus Induzierte Apoptose in Humanen und Caninen Zellen* [*Nicotine Affects the Apoptosis in Human and Canine Cells Induced by Influenza A Virus*] 1-52 (Dissertation 2003), http://deposit.ddb.de/cgi-bin/dokserv?idn=967996465&dok_var=d1&dok_ext=pdf &filename=967996465.pdf.
Kumon, "T4-Bacteriophage as a Surface Marker for Scanning Electron Microscopy," *Biomed Res.* 2(Suppl.):41-48 (1981).
Kuroda et al., "Retarded Processing of Influenza Virus Hemagglutinin in Insect Cells," *Virology* 180(1):159-65 (1991).
LaForce et al., "Diagnosis of Bacterial Meningitis by Gas-liquid Chromatography. II. Analysis of Spinal Fluid," *J. Infect. Dis.* 140(4):453-64 (1979).
Lai et al., "Genetic and Antigenic Analysis of the Influenza Virus Responsible for the 1992 Hong Kong Equine Influenza Epizootic," *Virology* 204(2):673-9 (1994).
Langford et al., "Copper-Zinc Superoxide Dismutase in *Haemophilus* Species," *J. Gen. Microbiol.* 138(3):517-22 (1992).
Larin et al., "Antiviral Activity of Gliotoxin," *Chemotherapia* 10(1):12-23 (1965).

Lemen et al., "Canine Parainfluenza Type 2 Bronchiolitis Increases Histamine Responsiveness in Beagle Puppies," *Am. Rev. Respir. Dis.* 141(1):199-207 (1990).

Leonov et al., "Enzyme Immunoassay System Based on the Antibody Fragments FAB-2 Used to Determine Influenza Virus Hemagglutinin," *Voprosy Virusologii* 32(4):498-502, at Abstract (1987).

Li et al., "[Preparation of Canine Multivalence Serum and Its Application]," *Zhongguo Mianylxue Zazhi* 21(7):521-523, at Abstract (2005), http://www.cqvip.com.

Lieberman et al., "Production of Antibody in the Canine Tracheal Pouch After Local and Systemic Influenza Immunization," *J. Immunol.* 109(4):864-9 (1972).

Lwoff & Pirosky, "Growth Factor for *Haemophilus ducreyi*," *Comptes Rendus Seances Societe Biologie Ses Filiales* 124:1169-71, at Abstract (1937).

Mark et al., "Nuclear Accumulation of Influenza Viral RNA Transcripts and the Effects of Cycloheximide, Actinomycin D, and α-Amanitin," *J. Virol.* 29(2):744-752 (1979).

Mayr et al., "Funktionell-synergistische Kombinationsvaccinen. Ein Neuer Impfstofftyp [Functional-synergic Combined Vaccines. A New Type of Vaccine]," *Zentralblatt fur Verterinarmedizin* 26B(3):222-238, at Abstract (1979).

McCaw et al., "Early Protection of Puppies Against Canine Parvovirus: A Comparison of Two Vaccines," *J. Am. Anim. Hosp. Assoc.* 33(3):244-250 (1997).

McGavin et al., "Evidence for Australia-wide Canine Parainfluenza Infection," *Austral. Vet. J.* 66(7):221 (1989).

Miyamoto et al., "Immunological Responses After Vaccination Pre- and Post-surgery in Dogs," *J. Vet. Med. Sci.* 57(1):29-32 (1995).

Mochizuki, "Growth Characteristics of Canine Pathogenic Viruses in MDCK Cells Cultured in RPMI 1640 Medium Without Animal Protein," *Vaccine* 24(11):1744-1748 (2006).

Mouzin et al., "Duration of Serologic Response to Five Viral Antigens in Dogs," *J. Am. Vet. Med. Assoc.* 224(1):55-60 (2004).

Willer et al., "Isolation, Sequencing and Phylogenetic Analysis of the Hemagglutinin, Neuraminidase and Nucleoprotein Genes of the Chilean Equine Influenza Virus Subtypes H7N7 and H3N8," *Biol. Res.* 38(1):55-67 (2005).

Niemi et al., "Neurological Syndrome in the Ferret (*Mustela putorius furo*)," *Vet. Record* 114(18):455-456 (1984).

Noll & Youngner, "Virus-Lipid Interactions. II. The Mechanism of Adsorption of Lipophilic Viruses to Water-insoluble Polar Lipids," *Virology* 8:319-43 (1959).

Ohmori et al., "Immunoblot Analysis for IgE-reactive Components of Fetal Calf Serum in Dogs That Developed Allergic Reactions After Non-rabies Vaccination," *Vet. Immunol Immunopathol.* 115(1-2):166-171 (2007).

Ohwada et al., "Distribution of the Antibody to Influenza C Virus in Dogs and Pigs in Yamagata Prefecture, Japan," *Microbiol. Immunol.* 31(12):1173-80 (1987).

Olsen et al., "*bcl-2* Alters Influenza Virus Yield, Spread, and Hemagglutinin Glycosylation," *J. Virol.* 70(1):663-6 (1996).

Osterhaus et al., "Antiviral Antibodies in Dogs in the Netherlands," *Zbl. Vet. Med. B* 24(2):123-133 (1977).

Ott et al., "Enhancement of Humoral Response Against Human Influenza Vaccine with the Simple Submicron Oil/Water Emulsion Adjuvant MF59," *Vaccine* 13(16):1557-62 (1995).

Oxburgh et al., "Equine Influenza Virus from the 1991 Swedish Epizootic Shows Major Genetic and Antigenic Divergence from the Prototype Virus," *Virus Res.* 28(3):263-72 (1993).

Oxford et al., "Non-responders to Egg Grown Influenza Vaccine Seroconvert After Booster Immunization with MDCK Cell Grown Vaccine," *Vaccine* 21(21-23):2743-46 (2003).

Packard & Grafton-Packard, "The Effect of Canine Parainfluenza Vaccine on the Spread of Tracheobronchial Coughs in a Boarding Kennel," *J. Am. Anim. Hosp. Assoc.* 15(2):241-244 (1979).

Palache et al., "Safety, Reactogenicity and Immunogenicity of Madin Darby Canine Kidney Cell-derived Inactivated Influenza Subunit Vaccine. A Meta-analysis of Clinical Studies," *Dev. Biol. Stand.* 98:115-125 (1999).

Paul et al., "Report of the American Animal Hospital Association (AAHA) Canine Vaccine Task Force: Executive Summary and 2003 Canine Vaccine Guidelines and Recommendations," *J. Am. Anim. Hosp. Assoc.* 39(2):119-131 (2003).

Povey, "In Vitro Antiviral Efficacy of Ribavirin Against Feline Calicivirus, Feline Viral Rhinotracheitis Virus, and Canine Parainfluenza Virus," *Am. J. Vet. Res.* 39(1):175-8 (1978).

Powell, "Use of Canine Adenovirus Type 2 Vaccine to Control Kennel Cough Syndrome," *Vet. Med. & Small Anim. Clinician* 74(6):801-804 (1979).

Prince & Smith, "Antigenic Studies on *Pasteurella multocida* Using Immunodiffusion Techniques. II. Relationships with Other Gram-negative Species," *J. Comp. Pathol.* 76(3):315-20 (1966).

Quan et al., "Canine Parainfluenza Type 2 and *Bordetella bronchiseptica* Infection Produces Increased Bronchoalveolar Lavage Thromboxane Concentrations in Beagle Puppies," *Prostaglandins Leukotrienes Essential Fatty Acids* 44(3):171-5 (1991).

Rao, "Prevalence of Influenza Virus Antibody in Dog and Goat Sera from Pune, 1977," *Indian J. Med. Res.* 76:59-61 (1982).

Reif et al., "Local and Systemic Cell-mediated Immunity in Viral Infection of the Canine Respiratory Tract," *Transplant. Proc.* 7(4):561-565 (1975).

Sanford et al., "Bacterial Adherence to Virus infected Cells: A Cell Culture Model of Bacterial Superinfection," *J. Infect. Dis.* 137(2):176-181 (1978).

Scheele & Blackburn, "Role of Mammalian RNase Inhibitor in Cell-free Protein Synthesis," *Proc. Nat'l Acad. Sci. USA* 76(10):4898-902 (1979).

Schulman et al., "Ocular Penetration of Flurbiprofen," *Invest. Ophthamol. Visual Sci.* 63, Abstract No. 24 (1980).

Senda et al., "Virus Content Test Without Using Antiserum for Canine Adenovirus and Canine Parainfluenza Virus in Canine Live Combined Vaccines," *40th Ann. Rep. Nat'l Vet. Assay Lab.* 11-15 (2003).

Shenderovich et al., "Selection of Influenza Virus Antigenic Variants in Cells of Different Hosts," *Voprosy Virusologii* 35(6):466-468, at Abstract (1990).

Shinya et al., "Adaptation of an H7N7 Equine Influenza A Virus in Mice," *J. Gen. Virol.* 88(2):547-553 (2007).

Sihvonen & Rikula, "Koirien Rokotukset [Vaccination of Dogs]," *Suomen Elainlaakarilehti* 98(11):597, 599-603, at Abstract (1992).

Smith, "Are We Vaccinating Too Much?," *J. Am. Vet. Med. Assoc.* 207(4):421-425 (1995).

Soma et al., "Antibody Testing Against Canine Coronavirus by Immunoperoxidase Plaque Staining," *Vet. Res. Commun.* 25(4):327-36 (2001).

Southern et al., "Identification of an Epitope on the P and V Proteins of Simian Virus 5 That Distinguishes Between Two Isolates with Different Biological Characteristics," *J. Gen. Virol.* 72(7):1551-1557 (1991).

Spriggs et al., "Fusion Glycoprotein of Human Parainfluenza Virus Type 3: Nucleotide Sequence of the Gene, Direct Identification of the Cleavage-activation Site, and Comparison with Other Paramyxoviruses," *Virology* 152(1):241-51 (1986).

Sprino & Harris, "Serologic Interference Study of a Canine Parvovirus, Distemper, Hepatitis, Parainfluenza L. canicola-icterohaemorrhagiae Vaccine," *Vet. Med. Small Anim. Clinician* 78(3):337-339 (1983).

Steele-Mortimer et al., "Flow Cytometric Analysis of Virus-infected Cells and Its Potential Use for Screening Antiviral Agents," *J. Virol. Meth.* 27(3):241-252 (1990).

Stridh et al., "Forsaljningsstatistik 1993-2002. Vacciner for Hund och Katt, del 2 [Sales Statistics of Vaccines for Dogs and Cats Between 1993 and 2002]," *Svensk Veterinartidning* 55(11):17-21, at Abstract (2003).

Sutton & Evans, "Kennel Cough—the Practitioner's View," *Vet. Pract.* 18(14):11-13 (1986).

Thiry et al., "Highly Pathogenic Avian Influenza H5N1 Virus in Cats and Other Carnivores," *Vet. Microbiol.* 122(1-2):25-31 (2007).

Thrusfield et al., "A Field Investigation of Kennel Cough: Efficacy of Vaccination," *J. Sm. Anim. Pract.* 30(10):550-560 (1989).

Timbol et al., "Detection of Canine Respiratory Disease Viral Antigens by Direct Fluorescent Antibody Technique," *Philippine J. Anim. Indust.* 35(1/4):79-89 (1980).

Toshach et al., "Hepatocellular Necrosis Associated with the Subcutaneous Injection of an Intranasal *Bordetella bronchiseptica*—Canine Parainfluenza Vaccine," *J. Am. Anim. Hosp. Assoc.* 33(2):126-8 (1997).
Ueland, "Outbreak of Kennel Cough in Norway," *Vet. Record* 124(24):642 (1989).
Ueland, "Serological, Bacteriological and Clinical Observations on an Outbreak of Canine Infectious Tracheobronchitis in Norway," *Vet. Record* 126(19):481-3 (1990).
Vahlenkamp & Harder, "Influenza Virus Infections in Mammals," *Berl. Münch. Tierärztl. Wochenschr.* 119(3-4):123-131 (2006).
Van Heerden et al., "An Investigation into the Health Status and Diseases of Wild Dogs (*Lycaon pictus*) in the Kruger National Park," *J. S. Afr. Vet. Assoc.* 66(1):18-27 (1995).
Von Grotthuss & Rychlewski, "Influenza Mutation from Equine to Canine," *Science* 311(5765):1241 (2006).
Waner et al., "Post-vaccination Evaluation of the Immunization Status of Puppies for Canine Parvo- and Distemper Viruses Using an In-clinic ELISA Test," *Isr. J. Vet. Med.* 58(4):104-108 (2003).
Wegrzyn & Kontor, "Correlation Between Virulent Canine Parainfluenza Viral Shedding and Presence of IgA in Nasal Secretions of Vaccinated Dogs," *Abstr. Ann. Mtg. Am. Soc. Microbiol.* 81:67, Abstract No. E75 (1981).
Wilbur et al., "Abortion and Death in Pregnant Bitches Associated with a Canine Vacine Contaminated with Bluetongue Virus," *J. Am. Vet. Med. Assoc.* 204(11):1762-1765 (1994).
Williamson & Jackson, "The Antiviral Activity of the Isoquinolines Famotine and Memotine in Respiratory Infections in Man," *Bull. Wld. Hlth. Org.* 41(3-5):665-70 (1969).
Windsor et al., "Molecular Detection of Microbes in Nasal Tissue of Dogs with Idiopathic Lymphoplasmacytic Rhinitis," *J. Vet. Intern. Med.* 20(2):250-6 (2006).
Wray et al., "Influenza-infected Madin Darby Canine Kidney Cells: Effect of Ribavirin on Ribonucleoprotein Synthesis and Nucleotide Pools," American Society for Microbiology, 83rd Annual Meeting (Mar. 1983).
Written Opinion of the International Searching Authority for PCT Patent Application No. PCT/US2007/066169 (Jul. 31, 2008).
Young & Parks, "Simian Virus 5 Is a Poor Inducer of Chemokine Secretion from Human Lung Epithelial Cells: Identification of Viral Mutants That Activate Interleukin-8 Secretion by Distinct Mechanisms," *J. Virol.* 77(12):7124-7130 (2003).
Zhimov et al., "Influenza Virus Matrix Protein M1 Interaction with Histones," *Mol. Biol.* 31(1):114-119 (1997).
Zhirnov et al., "Proteolytic Activation of Influenza WSN Virus in Cultured Cells Is Performed by Homologous Plasma Enzymes," *J. Gen. Virol.* 63(2):469-74 (1982).
Zuffa & Krobot, "Dokaz Protilatok Proti Virusom Infekcnej Laryngotracheitidy a Parainfluenzy 2 u Psov v Chovov na Uzemi Cssr [Detection of Antibodies Against Infectious Viral Laryngotracheitis and Parainfluenza 2 in Dogs Bred in Czechoslovakia]," *Veterinarni Medicina* 32(11)689-94, at Abstract (1987).
Zygraich et al.; "Langzeituntersuchung zur Immunogenität eines Kombinationsimpfstoffes für Hunde [Long-term Study on Immunogenicity of a Combined Vaccine for Dogs]," *Kleintierpraxis* 30(1):45-48, at Abstract (1985).
Genbank Accession No. AAA43101, Jul. 10, 2006.
Genbank Accession No. AAA43102, Jul. 10, 2006.
Genbank Accession No. AAA43103, Jul. 10, 2006.
Genbank Accession No. AAA43105, Jul. 10, 2006.
Genbank Accession No. AAA43107 , Jul. 10, 2006.
Genbank Accession No. AAA43109, Jul. 10, 2006.
Genbank Accession No. AAA43110, Jul. 10, 2006.
Genbank Accession No. AAA43112, Jul. 10, 2006.
Genbank Accession No. AAA43114, Jul. 10, 2006.
Genbank Accession No. AAA43164, Jul. 13, 2006.
Genbank Accession No. AAA62470, Sep. 17, 2004.
Genbank Accession No. AAB02560, Dec. 13, 2001.
Genbank Accession No. AAB27733, Sep. 30, 1993.
Genbank Accession No. AAB36975, Nov. 1, 2004.
Genbank Accession No. AAB36976, Nov. 1, 2004.
Genbank Accession No. AAB36977, Nov. 1, 2004.
Genbank Accession No. AAB36978, Nov. 1, 2004.
Genbank Accession No. AAB36979, Nov. 1, 2004.
Genbank Accession No. AAB36980, Jan. 1, 2004.
Genbank Accession No. AAQ90291, Oct. 6, 2003.
Genbank Accession No. AAX23575, Mar. 12, 2005.
Genbank Accession No. AAZ23560, Jan. 25, 2006.
Genbank Accession No. ABA39842, Jan. 25, 2006.
Genbank Accession No. ABA39843, Jan. 25, 2006.
Genbank Accession No. ABA39844, Jan. 25, 2006.
Genbank Accession No. ABA39845, Jan. 25, 2006.
Genbank Accession No. ABA39846, Jan. 25, 2006.
Genbank Accession No. ABA39847, Jan. 25, 2006.
Genbank Accession No. ABA39848, Jan. 25, 2006.
Genbank Accession No. ABA39849, Jan. 25, 2006.
Genbank Accession No. ABA39850, Jan. 25, 2006.
Genbank Accession No. ABA41538, Nov. 16, 2005.
Genbank Accession No. ABA42433, Jan. 25, 2006.
Genbank Accession No. ABA42434, Jan. 25, 2006.
Genbank Accession No. ABA42435, Jan. 25, 2006.
Genbank Accession No. ABA42436, Jan. 25, 2006.
Genbank Accession No. ABA42441, Jan. 25, 2006.
Genbank Accession No. ABA42442, Jan. 25, 2006.
Genbank Accession No. ABB17173, Oct. 29, 2005.
Genbank Accession No. ABF60576, Mar. 19, 2006.
Genbank Accession No. ABM21938, Dec. 29, 2006.
Genbank Accession No. ABM47075, Mar. 2, 2007.
Genbank Accession No. AF197241, Jan. 8, 2003.
Genbank Accession No. AF197242, Jan. 8, 2003.
Genbank Accession No. AF197243, Jan. 8, 2003.
Genbank Accession No. AF197244, Jan. 8, 2003.
Genbank Accession No. AF197245, Jan. 8, 2003.
Genbank Accession No. AF197247, Jan. 8, 2003.
Genbank Accession No. AF197248, Jan. 8, 2003.
Genbank Accession No. AF197249, Jan. 8, 2003.
Genbank Accession No. AJ223192, Apr. 15, 2005.
Genbank Accession No. AJ223193, Apr. 15, 2005.
Genbank Accession No. AJ223194, Apr. 15, 2005.
Genbank Accession No. AJ223195, Apr. 15, 2005.
Genbank Accession No. AY048077, Dec. 31, 2002.
Genbank Accession No. AY048078, Dec. 31, 2002.
Genbank Accession No. AY048079, Dec. 31, 2002.
Genbank Accession No. AY048080, Dec. 31, 2002.
Genbank Accession No. AY048081, Dec. 31, 2002.
Genbank Accession No. AY273167, Mar. 19, 2004.
Genbank Accession No. AY273168, Mar. 19, 2004.
Genbank Accession No. AY383755, Oct. 6, 2003.
Genbank Accession No. AY855341, Mar. 12, 2005.
Genbank Accession No. AY919314, Mar. 1, 2005.
Genbank Accession No. CAA48482, Apr. 18, 2002.
Genbank Accession No. CAA64893, Apr. 18, 2005.
Genbank Accession No. CAA64894, Apr. 18, 2005.
Genbank Accession No. CY018869, Dec. 29, 2006.
Genbank Accession No. D30678, Dec. 12, 2007.
Genbank Accession No. D30679, Dec. 12, 2007.
Genbank Accession No. D30680, Mar. 26, 2003.
Genbank Accession No. D30681, Dec. 12, 2007.
Genbank Accession No. D30683, Dec. 12, 2007.
Genbank Accession No. D30684, Dec. 12, 2007.
Genbank Accession No. D30686, Dec. 12, 2007.
Genbank Accession No. DQ124147, Jan. 25, 2006.
Genbank Accession No. DQ124152, Jan. 25, 2006.
Genbank Accession No. DQ124157, Jan. 25, 2006.
Genbank Accession No. DQ124160, Jan. 25, 2006.
Genbank Accession No. DQ124189, Jan. 25, 2006.
Genbank Accession No. DQ124190, Jan. 25, 2006.
Genbank Accession No. DQ124191, Jan. 25, 2006.
Genbank Accession No. DQ124192, Jan. 25, 2006.
Genbank Accession No. DQ124193, Jan. 25, 2006.
Genbank Accession No. DQ124194, Jan. 25, 2006.
Genbank Accession No. DQ124195, Jan. 25, 2006.
Genbank Accession No. DQ124196, Jan. 25, 2006.
Genbank Accession No. DQ124197, Jan. 25, 2006.
Genbank Accession No. DQ146419, Nov. 16, 2005.
Genbank Accession No. DQ222913, Oct. 29, 2005.

Genbank Accession No. EF117330, Mar. 2, 2007.
Genbank Accession No. EF541429.
Genbank Accession No. EF541430, Apr. 17, 2007.
Genbank Accession No. EF541432, Apr. 17, 2007.
Genbank Accession No. EF541433, Apr. 17, 2007.
Genbank Accession No. EF541434, Apr. 17, 2007.
Genbank Accession No. EF541437, Apr. 17, 2007.
Genbank Accession No. EF541438, Apr. 17, 2007.
Genbank Accession No. EF541439, Apr. 17, 2007.
Genbank Accession No. EF541440, Apr. 17, 2007.
Genbank Accession No. EF541441, Apr. 17, 2007.
Genbank Accession No. L27597, Sep. 17, 2004.
Genbank Accession No. L39913, Nov. 1, 2004.
Genbank Accession No. L39914, Nov. 1, 2004.
Genbank Accession No. L39915, Nov. 1, 2004.
Genbank Accession No. L39916, Nov. 1, 2004.
Genbank Accession No. L39917, Nov. 1, 2004.
Genbank Accession No. L39918, Nov. 1, 2004.
Genbank Accession No. M24718, Jul. 10, 2006.
Genbank Accession No. M24719, Jul. 10, 2006.
Genbank Accession No. M24722, Jul. 10, 2006.
Genbank Accession No. M24723, Jul. 10, 2006.
Genbank Accession No. M24724, Jul. 10, 2006.
Genbank Accession No. M24725, Jul. 10, 2006.
Genbank Accession No. M24726, Jul. 10, 2006.
Genbank Accession No. M24727, Jul. 10, 2006.
Genbank Accession No. M24728, Jul. 10, 2006.
Genbank Accession No. M29257, Jul. 13, 2006.
Genbank Accession No. M73773, May 19, 2006.
Genbank Accession No. P15658, Oct. 23, 2007.
Genbank Accession No. P16995, Oct. 23, 2007.
Genbank Accession No. P16996, Oct. 23, 2007.
Genbank Accession No. P16997, Oct. 23, 2007.
Genbank Accession No. P16998, Oct. 23, 2007.
Genbank Accession No. P16999, Oct. 23, 2007.
Genbank Accession No. P17001, Oct. 23, 2007.
Genbank Accession No. P17002, Oct. 23, 2007.
Genbank Accession No. P19699, Oct. 23, 2007.
Genbank Accession No. Q08011, Oct. 23, 2007.
Genbank Accession No. Q82559, Oct. 23, 2007.
Genbank Accession No. S64310, Sep. 30, 1993.
Genbank Accession No. U58195, Dec. 13, 2001.
Genbank Accession No. X68437, Apr. 18, 2005.
Genbank Accession No. X85085, Apr. 18, 2005.
Genbank Accession No. X85086, Apr. 18, 2005.
Genbank Accession No. X85088, Apr. 18, 2005.
Genbank Accession No. X85090, Apr. 18, 2005.
Genbank Accession No. X95637, Apr. 18, 2005.
Genbank Accession No. X95638, Apr. 18, 2005.
Genbank Accession No. Y14056, Nov. 14, 2006.
Genbank Accession No. Y14058, Nov. 14, 2006.
Genbank Accession No. Y14059, Nov. 14, 2006.
Genbank Accession No. Y14060, Nov. 14, 2006.

* cited by examiner

```
atatttctgt caatc atg aag aca acc att att tta ata cta ctg acc cat    51
              Met Lys Thr Thr Ile Ile Leu Ile Leu Leu Thr His
                1               5                  10 tgg gcc tac agt caa aac cca atc agt ggc aat aac aca gcc aca ctg    99
Trp Ala Tyr Ser Gln Asn Pro Ile Ser Gly Asn Asn Thr Ala Thr Leu
         15                  20                  25 tgt ctg gga cac cat gca gta gca aat gga aca ttg gta aaa aca atg   147
Cys Leu Gly His His Ala Val Ala Asn Gly Thr Leu Val Lys Thr Met
     30                  35                  40 agt gat gat caa att gag gta aca aat gct aca gaa tta gtt cag agc   195
Ser Asp Asp Gln Ile Glu Val Thr Asn Ala Thr Glu Leu Val Gln Ser
 45                  50                  55                  60 att tca atg ggg aaa ata tgc aac aaa tca tat aga att cta gat gga   243
Ile Ser Met Gly Lys Ile Cys Asn Lys Ser Tyr Arg Ile Leu Asp Gly
             65                  70                  75 aga aat tgc aca tta ata gat gca atg cta gga gac ccc cac tgt gac   291
Arg Asn Cys Thr Leu Ile Asp Ala Met Leu Gly Asp Pro His Cys Asp
             80                  85                  90 gcc ttt cag tat gag agt tgg gac ctc ttt ata gaa aga agc aac gct   339
Ala Phe Gln Tyr Glu Ser Trp Asp Leu Phe Ile Glu Arg Ser Asn Ala
             95                 100                 105 ttc agc aat tgc tac cca tat gac atc cct gac tat aca tcg ctc cga   387
Phe Ser Asn Cys Tyr Pro Tyr Asp Ile Pro Asp Tyr Thr Ser Leu Arg
    110                 115                 120 tcc att gta gca tcc tca gga gca gtg gaa ttc aca gca gag gga ttc   435
Ser Ile Val Ala Ser Ser Gly Ala Val Glu Phe Thr Ala Glu Gly Phe
125                 130                 135                 140 aca tgg aca ggt gtc act caa aac gga aga agt gga gcc tgc aaa agg   483
Thr Trp Thr Gly Val Thr Gln Asn Gly Arg Ser Gly Ala Cys Lys Arg
                145                 150                 155 gga tca gcc gat agt ttc ttt agc cga ctg aat tgg cta aca aaa tct   531
Gly Ser Ala Asp Ser Phe Phe Ser Arg Leu Asn Trp Leu Thr Lys Ser
            160                 165                 170 gga agc tct tac ccc aca ttg aat gtg aca atg cct aac aat aaa aat   579
Gly Ser Ser Tyr Pro Thr Leu Asn Val Thr Met Pro Asn Asn Lys Asn
        175                 180                 185 ttc gac aag cta tac atc tgg ggg att cat cac ccg agc tca aat caa   627
Phe Asp Lys Leu Tyr Ile Trp Gly Ile His His Pro Ser Ser Asn Gln
    190                 195                 200 gag cag aca aaa ttg tac atc caa gaa tca gga cga gta aca gtc tca   675
Glu Gln Thr Lys Leu Tyr Ile Gln Glu Ser Gly Arg Val Thr Val Ser
205                 210                 215                 220
```

FIG. 1A

```
aca aaa aga agt caa caa aca ata atc cct aac atc gga tct aga ccg      723
Thr Lys Arg Ser Gln Gln Thr Ile Ile Pro Asn Ile Gly Ser Arg Pro
            225                 230                 235 ttg gtc aga ggt caa tca ggc agg ata agc ata tac tgg acc att gta      771
Leu Val Arg Gly Gln Ser Gly Arg Ile Ser Ile Tyr Trp Thr Ile Val
            240                 245                 250 aaa cct gga gat atc cta atg ata aac agt aat ggc aac tta gtt gca      819
Lys Pro Gly Asp Ile Leu Met Ile Asn Ser Asn Gly Asn Leu Val Ala
            255                 260                 265 ccg cgg gga tat ttt aaa ttg aac aca ggg aaa agc tct gta atg aga      867
Pro Arg Gly Tyr Phe Lys Leu Asn Thr Gly Lys Ser Ser Val Met Arg
    270                 275                 280 tcc gat gta ccc ata gac att tgt gtg tct gaa tgt att aca cca aat      915
Ser Asp Val Pro Ile Asp Ile Cys Val Ser Glu Cys Ile Thr Pro Asn
285                 290                 295                 300 gga agc atc tcc aac gac aag cca ttc caa aat gtg aac aaa gtt aca      963
Gly Ser Ile Ser Asn Asp Lys Pro Phe Gln Asn Val Asn Lys Val Thr
                305                 310                 315 tat gga aaa tgc ccc aag tat atc agg caa aac act tta aag ctg gcc     1011
Tyr Gly Lys Cys Pro Lys Tyr Ile Arg Gln Asn Thr Leu Lys Leu Ala
            320                 325                 330 act ggg atg agg aat gta cca gaa aag caa acc aga gga atc ttt gga     1059
Thr Gly Met Arg Asn Val Pro Glu Lys Gln Thr Arg Gly Ile Phe Gly
            335                 340                 345 gca ata gcg gga ttc atc gaa aac ggc tgg gaa gga atg gtt gat ggg     1107
Ala Ile Ala Gly Phe Ile Glu Asn Gly Trp Glu Gly Met Val Asp Gly
    350                 355                 360 tgg tat ggg ttc cga tat caa aac tct gaa gga aca ggg caa gct gca     1155
Trp Tyr Gly Phe Arg Tyr Gln Asn Ser Glu Gly Thr Gly Gln Ala Ala
365                 370                 375                 380 gat cta aag agc act caa gca gcc atc gac cag att aat gga aag tta     1203
Asp Leu Lys Ser Thr Gln Ala Ala Ile Asp Gln Ile Asn Gly Lys Leu
            385                 390                 395 aac aga gtg att gaa aga acc aat gag aaa ttc cat caa ata gag aag     1251
Asn Arg Val Ile Glu Arg Thr Asn Glu Lys Phe His Gln Ile Glu Lys
            400                 405                 410 gaa ttc tca gaa gta gaa gga aga att cag gac ttg gag aaa tat gta     1299
Glu Phe Ser Glu Val Glu Gly Arg Ile Gln Asp Leu Glu Lys Tyr Val
            415                 420                 425 gaa gac acc aaa ata gac cta tgg tcc tac aat gca gaa ttg ctg gtg     1347
Glu Asp Thr Lys Ile Asp Leu Trp Ser Tyr Asn Ala Glu Leu Leu Val
    430                 435                 440
```

FIG. 1B

```
gct cta gaa aat caa cat aca att gac tta aca gat gca gaa atg aat    1395
Ala Leu Glu Asn Gln His Thr Ile Asp Leu Thr Asp Ala Glu Met Asn
445             450                 455                 460 aaa tta ttt gag aag act aga cgc cag tta aga gaa aac gca gaa gac    1443
Lys Leu Phe Glu Lys Thr Arg Arg Gln Leu Arg Glu Asn Ala Glu Asp
            465                 470                 475 atg gga ggt gga tgt ttc aag att tac cac aaa tgt gat aat gca tgc    1491
Met Gly Gly Gly Cys Phe Lys Ile Tyr His Lys Cys Asp Asn Ala Cys
                480                 485                 490 att gaa tca ata aga act gga aca tat gac cat tac ata tac aga gat    1539
Ile Glu Ser Ile Arg Thr Gly Thr Tyr Asp His Tyr Ile Tyr Arg Asp
            495                 500                 505 gaa gca tta aac aac cga ttt cag atc aaa ggt gta gag ttg aaa tca    1587
Glu Ala Leu Asn Asn Arg Phe Gln Ile Lys Gly Val Glu Leu Lys Ser
        510                 515                 520 ggc tac aaa gat tgg ata ctg tgg att tca ttc gcc ata tca tgc ttc    1635
Gly Tyr Lys Asp Trp Ile Leu Trp Ile Ser Phe Ala Ile Ser Cys Phe
525                 530                 535                 540 tta att tgc gtt gtt cta ttg ggt ttc att atg tgg gct tgc caa aaa    1683
Leu Ile Cys Val Val Leu Leu Gly Phe Ile Met Trp Ala Cys Gln Lys
                545                 550                 555 ggc aac atc aga tgc aac att tgc att tga gtaaactgat agtta           1728
Gly Asn Ile Arg Cys Asn Ile Cys Ile
                560                 565
```

FIG. 1C

CANINE INFLUENZA VIRUS

This application claims the benefit of U.S. Provisional Patent Application Ser. No. 60/789,795, filed Apr. 6, 2006, which is hereby incorporated by reference in its entirety.

FIELD OF THE INVENTION

The present invention relates to an isolated canine influenza virus. The present invention also relates to an isolated nucleic acid encoding a hemagglutinin of the canine influenza virus, as well as to corresponding isolated hemagglutinin protein or polypeptide. The present invention further relates to the use of the isolated canine influenza virus, the hemagglutinin nucleic acid molecules, and the corresponding hemagglutinin proteins or polypeptides in drugs, vaccines, and diagnostic tests.

BACKGROUND OF THE INVENTION

Canine influenza is a highly contagious respiratory infection of dogs that is caused by a virus. The canine influenza virus is closely related to the virus that causes equine influenza and it is thought that the equine influenza virus mutated to produce the canine influenza virus.

Two clinical syndromes have been seen in dogs infected with the canine influenza virus—a mild form of the disease and a more severe form that is accompanied by pneumonia. Dogs suffering with the mild form of canine influenza develop a soft, moist cough that persists for 10 to 30 days. Some dogs have a dry cough similar to the "kennel cough" caused by *Bordetella bronchiseptica*/parainfluenza virus complex. For this reason, canine influenza virus infections are frequently mistaken for "kennel cough." Dogs with the mild form of influenza may also have a thick nasal discharge, which is usually caused by a secondary bacterial infection. Dogs with the severe form of canine influenza develop high fevers (104° F. to 106° F.) and have clinical signs of pneumonia, such as increased respiratory rates and effort. Pneumonia may be due to a secondary bacterial infection.

Because this is a newly emerging disease, almost all dogs, regardless of breed or age, are susceptible to infection and have no immunity. Virtually all dogs that are exposed to the virus become infected and nearly 80% show clinical signs of disease. Fortunately, most affected dogs have the mild form. Fatal cases of pneumonia resulting from infection with canine influenza virus have been reported in dogs, but the fatality rate (5% to 8%) has been low so far.

The first recognized outbreak of canine influenza in the world is believed to have occurred in racing greyhounds in January 2004 at a track in Florida. From June to August of 2004, outbreaks of respiratory disease were reported at 14 tracks in 6 states (Alabama, Arkansas, Florida, Kansas, Texas, and West Virginia). Between January and May of 2005, outbreaks occurred at 20 tracks in 11 states (Arizona, Arkansas, Colorado, Florida, Iowa, Kansas, Massachusetts, Rhode Island, Texas, West Virginia, and Wisconsin). Infection has also been confirmed in pet dogs in California, Connecticut, Florida, Georgia, Massachusetts, North Carolina, New Jersey, New York, Ohio, Oregon, Pennsylvania, Washington State, and Washington, DC. These cases occurred in animal shelters, humane societies, rescue groups, pet stores, boarding kennels, and veterinary clinics.

A critical aspect of the canine influenza virus situation in dogs is the continued isolation of the virus as it moves through the canine population. While PCR detection of the virus may be useful in the treatment of the patient, simply identifying the presence of the virus does little for understanding how the virus may be changing as it continues to encounter susceptible dogs. Even with the introduction of vaccines, sequence analysis of the isolates will be needed to determine whether canine influenza virus changes as do human influenzas or does it follow the more conservative path of its parent virus equine influenza. Samples need to be forwarded to laboratories that are capable of isolating the virus so that strains are available for genetic analysis.

There is a need for rapid tests for diagnosis of acute canine influenza virus infection. Diagnosis may be confirmed through serologic testing. Antibodies to canine influenza virus may be detected as early as seven days after onset of clinical signs. There is also a need for vaccines or other treatment methods against canine influenza virus.

The present invention is directed to overcoming the deficiencies in the prior art.

SUMMARY OF THE INVENTION

The present invention relates to an isolated canine influenza virus. In one embodiment, the isolated canine influenza virus contains a hemagglutinin gene having a nucleotide sequence of SEQ ID NO:1. In another embodiment, the isolated canine influenza virus contains an isolated nucleic acid molecule that encodes a hemagglutinin having an amino acid sequence of SEQ ID NO:2. The present invention also relates to a vaccine for canine influenza virus, where the vaccine includes the isolated canine influenza virus of the present invention and a pharmaceutically-acceptable carrier. Methods of using the isolated canine influenza virus to induce an immune response against canine influenza virus in a canine subject are also disclosed.

The present invention also relates to an isolated nucleic acid molecule encoding a hemagglutinin of a canine influenza virus. In one embodiment, the encoded hemagglutinin is a protein or polypeptide having an amino acid sequence of SEQ ID NO:2. In another embodiment, the isolated nucleic acid molecule has a nucleotide sequence of SEQ ID NO:1. In yet another embodiment, the isolated nucleic acid molecule has a nucleotide coding sequence corresponding to bases 16 through 1710 of SEQ ID NO:1 (with bases 1711 through 1713 representing a STOP codon). The isolated nucleic acid molecules can be inserted as heterologous DNA in an expression vector forming a recombinant DNA expression system for producing the proteins or polypeptides. Likewise, the heterologous DNA, usually inserted in an expression vector to form a recombinant DNA expression system, can be incorporated in a cell to achieve this objective.

The present invention further relates to an isolated canine influenza virus hemagglutinin protein or polypeptide. In one embodiment, the isolated canine influenza virus hemagglutinin protein or polypeptide has an amino acid sequence of SEQ ID NO:2. In another embodiment, the isolated protein or polypeptide is encoded by a nucleic acid molecule having a nucleotide sequence of SEQ ID NO:1. In yet another embodiment, the isolated protein or polypeptide is encoded by a nucleic acid molecule having a nucleotide sequence corresponding to bases 16 through 1710 of SEQ ID NO:1. The isolated proteins or polypeptides of the present invention can be combined with a pharmaceutically-acceptable carrier to form a vaccine or used alone for administration to canine subjects, for preventing onset of disease resulting from infection by a canine influenza virus. Alternatively, each of the proteins or polypeptides of the present invention can be used to raise an antibody or a binding portion thereof. The antibody or binding portion thereof may be used alone or combined with a pharmaceutically-acceptable carrier to treat canine subjects already exposed to a canine influenza virus to induce a passive immunity to prevent disease occurrence.

The proteins or polypeptides of the present invention or the antibodies or binding portions thereof raised against them can also be utilized in a method for detection of a canine influenza virus in a sample of tissue or body fluids. When the proteins or polypeptides are utilized, they are provided as an antigen. Any reaction with the antigen or the antibody is detected using an assay system which indicates the presence of a canine influenza virus in the sample. Alternatively, a canine influenza virus can be detected in such a sample by providing a nucleotide sequence of the isolated nucleic acid molecules of the present invention as a probe in a nucleic acid hybridization assay or a gene amplification detection procedure (e.g., using a polymerase chain reaction procedure). Any reaction with the probe is detected so that the presence of a canine influenza virus in the sample is indicated.

Isolation of the isolated canine influenza virus, the nucleic acid molecules encoding the hemagglutinin of the isolated canine influenza virus, and the encoded hemagglutinin protein or polypeptide of the present invention constitutes a significant advance in the study, treatment, and detection of canine influenza viruses. The use of the isolated canine influenza virus, the nucleic acid molecules encoding the hemagglutinin of the isolated canine influenza virus, and the encoded hemagglutinin protein or polypeptide of the present invention in vaccines and in detection methods are useful for the treatment and diagnosis of canine influenza viruses. The proteins or polypeptides utilized in the vaccine, or used to produce the pharmaceutical agent, can be produced at high levels using recombinant DNA technology.

In diagnostic applications, the nucleic acid molecules and proteins or polypeptides of the present invention, as well as antibodies and binding portions thereof against them, permit rapid determination of whether a particular individual canine subjects is infected with a canine influenza virus. Moreover, such detection can be carried out without requiring an examination of the individual canine subject being tested for an antibody response.

BRIEF DESCRIPTION OF THE DRAWINGS

FIGS. 1A-1C show the nucleotide sequence (SEQ ID NO:1) of an isolated nucleic acid molecule that encodes a hemagglutinin of an isolated canine influenza virus (particularly of the A/canine/NY/05 strain of the canine influenza virus). FIGS. 1A-1C also show the amino acid sequence (SEQ ID NO:2) of the encoded hemagglutinin protein or polypeptide of the isolated canine influenza virus. As shown in FIGS. 1A-1C, in one aspect of the present invention, the hemagglutinin protein or polypeptide can be encoded by bases 16 through 1710 of SEQ ID NO:1 (with bases 1711 through 1713 representing a STOP codon).

DETAILED DESCRIPTION OF THE INVENTION

The present invention relates to an isolated canine influenza virus. In one embodiment, the isolated canine influenza virus contains a hemagglutinin gene having a nucleotide sequence of SEQ ID NO:1 (see below for description of SEQ ID NO:1). In another embodiment, the isolated canine influenza virus contains an isolated nucleic acid molecule that encodes a hemagglutinin having an amino acid sequence of SEQ ID NO:2 (see below for description of SEQ ID NO:2). In a further embodiment, the isolated canine influenza virus of the present invention corresponds to canine influenza virus strain "A/canine/NY/05" (also referred to as "A/canine/NY/115809/05" or "A/canine/New York/05" or other variations well known to those of skill in the art). The isolated canine influenza virus can be in a live form, a live-attenuated form (i.e., live but weakened form), an inactive form, and/or in a recombinant form. These forms of the isolated canine influenza virus can be made by those of ordinary skill in the art by using procedures well known in the field of virology and vaccine production.

The present invention also relates to a vaccine for canine influenza virus, where the vaccine includes the isolated canine influenza virus (described herein) of the present invention and a pharmaceutically-acceptable carrier. Suitable pharmaceutically-acceptable carriers are described herein below. The vaccine can include various forms of the canine influenza virus of the present invention, including live, live-attenuated (i.e., live but weakened), inactive, and/or recombinant forms of the isolated canine influenza virus. The vaccine containing the isolated canine influenza virus of the present invention can be used to inhibit onset of canine influenza disease in a canine subject who has been contacted with various canine influenza virus strains, including, without limitation, canine influenza virus strains such as A/canine/New York/03, A/canine/New York/05, A/canine/Florida/03, A/canine/Florida/04, A/canine/Florida/43/04, A/canine/Florida/242/03, A/canine/Texas/04, A/canine/Texas/1/04, A/canine/Iowa/13628/05, and variants thereof.

The present invention also relates to methods of using the isolated canine influenza virus to induce an immune response against canine influenza virus in a canine subject. This method involves administering to the canine subject an effective immunizing amount of the vaccine containing the isolated canine influenza virus of the present invention. As described previously, the isolated canine influenza virus used in the vaccine can be in a live form, a live-attenuated form (i.e., live but weakened form), an inactive form, and/or in a recombinant form, using procedures well known in the field of virology and vaccine production. The vaccine can be administered using procedures well known in the art, including, without limitation, procedures involving oral, intradermal, intramuscular, intraperitoneal, intravenous, subcutaneous, and/or intranasal administration of the vaccine. These methods of using the isolated canine influenza virus to induce an immune response in a canine subject can be effective various strains of canine influenza virus, including, without limitation, strains described in the art as A/canine/New York/03, A/canine/New York/05, A/canine/Florida/03, A/canine/Florida/04, A/canine/Florida/43/04, A/canine/Florida/242/03, A/canine/Texas/04, A/canine/Texas/1/04, A/canine/Iowa/13628/05, and variants thereof.

The present invention also relates to an isolated nucleic acid molecule encoding a hemagglutinin of a canine influenza virus. In one embodiment, the isolated nucleic acid molecule of the present invention has a nucleotide sequence corresponding to SEQ ID NO:1 as follows:

```
atatttctgt caatcatgaa gacaaccatt attttaatac tactgaccca ttgggcctac    60
agtcaaaacc caatcagtgg caataacaca gccacactgt gtctgggaca ccatgcagta   120
gcaaatggaa cattggtaaa aacaatgagt gatgatcaaa ttgaggtaac aaatgctaca   180
```

```
                               -continued
gaattagttc agagcatttc aatggggaaa atatgcaaca aatcatatag aattctagat    240
ggaagaaatt gcacattaat agatgcaatg ctaggagacc cccactgtga cgcctttcag    300
tatgagagtt gggacctctt tatagaaaga agcaacgctt tcagcaattg ctacccatat    360
gacatccctg actatacatc gctccgatcc attgtagcat cctcaggagc agtggaattc    420
acagcagagg gattcacatg gacaggtgtc actcaaaacg gaagaagtgg agcctgcaaa    480
aggggatcag ccgatagttt ctttagccga ctgaattggc taacaaaatc tggaagctct    540
taccccacat tgaatgtgac aatgcctaac aataaaaatt tcgacaagct atacatctgg    600
gggattcatc acccgagctc aaatcaagag cagacaaaat tgtacatcca agaatcagga    660
cgagtaacag tctcaacaaa aagaagtcaa caaacaataa tccctaacat cggatctaga    720
ccgttggtca gaggtcaatc aggcaggata agcatatact ggaccattgt aaaacctgga    780
gatatcctaa tgataaacag taatggcaac ttagttgcac cgcggggata ttttaaattg    840
aacacaggga aaagctctgt aatgagatcc gatgtaccca tagacatttg tgtgtctgaa    900
tgtattacac caaatggaag catctccaac gacaagccat tccaaaatgt gaacaaagtt    960
acatatggaa aatgccccaa gtatatcagg caaaacactt taaagctggc cactgggatg   1020
aggaatgtac cagaaaagca aaccagagga atctttggag caatagcggg attcatcgaa   1080
aacggctggg aaggaatggt tgatgggtgg tatgggttcc gatatcaaaa ctctgaagga   1140
acagggcaag ctgcagatct aaagagcact caagcagcca tcgaccagat taatggaaag   1200
ttaaacagag tgattgaaag aaccaatgag aaattccatc aaatagagaa ggaattctca   1260
gaagtagaag aagaattca ggacttggag aaatatgtag aagacaccaa aatagaccta   1320
tggtcctaca atgcagaatt gctggtggct ctagaaaatc aacatacaat tgacttaaca   1380
gatgcagaaa tgaataaatt atttgagaag actagacgcc agttaagaga aaacgcagaa   1440
gacatgggag gtggatgttt caagatttac cacaaatgtg ataatgcatg cattgaatca   1500
ataagaactg aacatatga ccattacata tacagagatg aagcattaaa caaccgattt   1560
cagatcaaag gtgtagagtt gaaatcaggc tacaaagatt ggatactgtg gatttcattc   1620
gccatatcat gcttcttaat ttgcgttgtt ctattgggtt tcattatgtg ggcttgccaa   1680
aaaggcaaca tcagatgcaa catttgcatt tgagtaaact gatagtta                1728
```

In another embodiment, the isolated nucleic acid molecule of the present invention encodes a hemagglutinin of a canine influenza virus, where the hemagglutinin has a protein or polypeptide having an amino acid sequence of SEQ ID NO:2. In another embodiment, the isolated nucleic acid molecule encoding the hemagglutinin of a canine influenza virus can include a nucleotide coding sequence corresponding to bases 16 through 1710 of SEQ ID NO:1 (where bases 1711 through 1713 of SEQ ID NO:1 correspond to a STOP codon). In yet another embodiment, the isolated nucleic acid molecule of the present invention encodes a hemagglutinin from canine influenza virus strain A/canine/NY/05.

The present invention also relates to an isolated canine influenza virus hemagglutinin protein or polypeptide. In one embodiment, the isolated canine influenza virus hemagglutinin protein or polypeptide has an amino acid sequence of SEQ ID NO:2, which is described as follows:

```
Met Lys Thr Thr Ile Ile Leu Ile Leu Leu Thr His Trp Ala Tyr Ser
 1               5                   10                  15

Gln Asn Pro Ile Ser Gly Asn Asn Thr Ala Thr Leu Cys Leu Gly His
                20                  25                  30

His Ala Val Ala Asn Gly Thr Leu Val Lys Thr Met Ser Asp Asp Gln
            35                  40                  45

Ile Glu Val Thr Asn Ala Thr Glu Leu Val Gln Ser Ile Ser Met Gly
        50                  55                  60
```

-continued

```
Lys Ile Cys Asn Lys Ser Tyr Arg Ile Leu Asp Gly Arg Asn Cys Thr
 65                  70                  75                  80

Leu Ile Asp Ala Met Leu Gly Asp Pro His Cys Asp Ala Phe Gln Tyr
             85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Thr Ser Leu Arg Ser Ile Val Ala
        115                 120                 125

Ser Ser Gly Ala Val Glu Phe Thr Ala Glu Gly Phe Thr Trp Thr Gly
130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
210                 215                 220

Gln Gln Thr Ile Ile Pro Asn Ile Gly Ser Arg Pro Leu Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
                485                 490                 495
```

-continued

```
Arg Thr Gly Thr Tyr Asp His Tyr Ile Tyr Arg Asp Glu Ala Leu Asn
            500             505             510

Asn Arg Phe Gln Ile Lys Gly Val Glu Leu Lys Ser Gly Tyr Lys Asp
        515             520             525

Trp Ile Leu Trp Ile Ser Phe Ala Ile Ser Cys Phe Leu Ile Cys Val
    530             535             540

Val Leu Leu Gly Phe Ile Met Trp Ala Cys Gln Lys Gly Asn Ile Arg
545             550             555             560

Cys Asn Ile Cys Ile
                565
```

The isolated canine influenza virus hemagglutinin protein or polypeptide of the present invention (having amino acid sequence of SEQ ID NO:2) has 565 amino acid residues and has an estimated molecular weight of approximately 63.66 kilodaltons (based on molecular weight calculators well known in the art). In one embodiment, the isolated canine influenza virus hemagglutinin protein or polypeptide of the present invention is encoded by a nucleic acid molecule having a nucleotide sequence of SEQ ID NO:1. More particularly, in another embodiment, the isolated canine influenza virus hemagglutinin protein or polypeptide of the present invention is encoded by a nucleic acid molecule having a nucleotide sequence corresponding to bases 16 through 1710 of SEQ ID NO:1 (with bases 1711 through 1713 of SEQ ID NO:1 corresponding to a STOP codon) (see FIG. 1). The isolated canine influenza virus hemagglutinin protein or polypeptide of the present invention can be in recombinant form and can be in purified form. In yet another embodiment, the isolated canine influenza virus hemagglutinin protein or polypeptide of the present invention can be from the canine influenza virus strain A/canine/NY/05. In still another embodiment, a suitable isolated canine influenza virus hemagglutinin protein or polypeptide of the present invention can have an amino acid sequence that is at least 80%, 85%, 90%, 95%, 96%, 97%, 98%, or 99% similar to the amino acid sequence of SEQ ID NO:2. Methods for determining sequence similarity of two different amino acid sequences are well known in the art of molecular biology.

Also suitable as an isolated nucleic acid molecule according to the present invention is an isolated nucleic acid molecule including at least 20 contiguous nucleic acid residues that hybridize to a nucleic acid having a nucleotide sequence of SEQ ID NO:1, or complements of SEQ ID NO:1, under stringent conditions (described more fully below). In another embodiment, a suitable isolated nucleic acid molecule of the present invention has a nucleotide sequence that is at least 80%, 85%, 90%, 95%, 96%, 97%, 98%, or 99% homologous to the nucleotide sequence of SEQ ID NO:1. Homologous nucleotide sequences can be detected by selectively hybridizing to each other. Selectively hybridizing is used herein to mean hybridization of DNA or RNA probes from one sequence to the "homologous" sequence under stringent conditions which are characterized by a hybridization buffer comprising 2×SSC, 0.1% SDS at 56° C. (Ausubel et al., eds., Current Protocols in Molecular Biology, Vol. I, New York: Greene Publishing Associates, Inc. and John Wiley & Sons, Inc., p. 2.10.3 (1989), which is hereby incorporated by reference in its entirety). Another example of suitable stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 µg/ml Escherichia coli DNA. In one embodiment, the present invention is directed to isolated nucleic acid molecules having nucleotide sequences containing at least 20 contiguous nucleic acid residues that hybridize to the nucleic acid molecules of the present invention, namely, SEQ ID NO:1, under stringent conditions including 50 percent formamide at 42° C.

Fragments of the above canine influenza virus hemagglutinin proteins or polypeptides are encompassed by the present invention.

The proteins or polypeptides of the present invention are preferably produced in purified form by conventional techniques. To isolate the proteins or polypeptides, a protocol involving a host cell such as Escherichia coli may be used, in which protocol the Escherichia coli host cell carrying a recombinant plasmid is propagated, homogenized, and the homogenate is centrifuged to remove bacterial debris. The supernatant is then subjected to sequential ammonium sulfate precipitation. The fraction containing the proteins or polypeptides of the present invention are subjected to gel filtration in an appropriately sized dextran or polyacrylamide column to separate the proteins or polypeptides. If necessary, the protein fraction may be further purified by high performance liquid chromatography (HPLC).

Fragments of the proteins or polypeptides of the present invention can be produced by digestion of a full-length elicitor protein with proteolytic enzymes like chymotrypsin or Staphylococcus proteinase A, or trypsin. Different proteolytic enzymes are likely to cleave the proteins or polypeptides of the present invention at different sites based on the amino acid sequence of the proteins or polypeptides. Some of the fragments that result from proteolysis may be active elicitors of resistance.

In another approach, based on knowledge of the primary structure of the protein or polypeptide, fragments of the genes encoding the proteins or polypeptides of the present invention may be synthesized by using the polymerase chain reaction (PCR) technique together with specific sets of primers chosen to represent particular portions of the protein or polypeptide of interest. These then would be cloned into an appropriate vector for expression of a truncated peptide or protein.

Chemical synthesis can also be used to make suitable fragments. Such a synthesis is carried out using known amino acid sequences for the protein or polypeptide being produced. Alternatively, subjecting a full length protein or polypeptide of the present invention to high temperatures and pressures will produce fragments. These fragments can then be separated by conventional procedures (e.g., chromatography, SDS-PAGE).

Variants may also (or alternatively) be made, for example, by the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The protein or polypeptide of the present invention is preferably produced in purified form (preferably at least about 80%, more preferably 90%, pure) by conventional techniques. Typically, the protein or polypeptide of the present invention is secreted into the growth medium of host cells which express a functional type III secretion system capable of secreting the protein or polypeptide of the present invention. Alternatively, the protein or polypeptide of the present invention is produced but not secreted into growth medium of recombinant host cells (e.g., *Escherichia coli*). In such cases, to isolate the protein, the host cell (e.g., *Escherichia coli*) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The nucleic acid molecule encoding the proteins or polypeptides of the present invention can be incorporated in cells using conventional recombinant nucleic acid technology. Generally, this involves inserting the nucleic acid molecule into an expression system to which the nucleic acid molecule is heterologous (i.e., not normally present). The heterologous nucleic acid molecule is inserted into the expression system or vector in sense orientation and correct reading frame. The vector contains the necessary elements for the transcription and translation of the inserted protein-coding sequences. Thus, the present invention also relates to a nucleic acid (e.g. DNA) construct containing the nucleic acid molecule of the present invention, which is operably linked to both a 5' promoter and a 3' regulatory region (i.e., transcription terminator) capable of affording transcription and expression of the encoded proteins or polypeptides of the present invention in host cells or host organisms.

The present invention also relates to an expression vector containing a nucleic acid molecule encoding the proteins or polypeptides of the present invention. The nucleic acid molecules of the present invention may be inserted into any of the many available expression vectors using reagents that are well known in the art. In preparing a nucleic acid molecule vector for expression, the various nucleic acid molecule sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation.

Suitable vectors for practicing the present invention include, but are not limited to, the following viral vectors such as lambda vector system gt11, gtWES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK ± or KS ± (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology*. 185:60-89 (1990), which is hereby incorporated by reference in its entirety), and any derivatives thereof. Any appropriate vectors now known or later described for genetic transformation are suitable for use with the present invention. Recombinant molecules can be introduced into cells via transformation, particularly transduction, conjugation, mobilization, or electroporation. The nucleic acid molecule sequences are cloned into the vector using standard cloning procedures in the art, as described by Maniatis et al., *Molecular Cloning: A Laboratory Manual*, Cold Springs Harbor, N.Y.: Cold Springs Laboratory (1982), which is hereby incorporated by reference in its entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is generally desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism.

An inducible promoter is a promoter that is capable of directly or indirectly activating transcription of one or more DNA sequences or genes in response to an inducer. In the absence of an inducer, the DNA sequences or genes will not be transcribed.

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. *Current Protocols in Molecular Biology*, New York, N.Y.: John Wiley & Sons. (1989), which are hereby incorporated by reference in their entirety.

Once the DNA construct of the present invention has been prepared, it is ready to be incorporated into a host cell. Accordingly, another aspect of the present invention relates to a method of making a recombinant cell. Basically, this method is carried out by transforming a host cell with a DNA construct of the present invention under conditions effective to yield transcription of the DNA molecule in the host cell. Recombinant molecules can be introduced into cells via transformation, particularly transduction, conjugation, mobilization, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like.

Generally, the mammalian immune system responds to infection by pathogenic bacteria by producing antibodies that bind to specific proteins or carbohydrates on the bacterial surface. The antibodies stimulate binding to macrophages which have receptors that bind to the F<c> region of the antibodies. Other serum proteins, called complement, coat the foreign particle and stimulate their ingestion by binding to specific surface receptors on the macrophage. Once the particle is bound to the surface of the macrophage, the sequential process of ingestion begins by continual apposition of a segment of the plasma membrane to the particle surface. Surface receptors on the membranes then interact with ligands distributed uniformity over the particle surface to link the surfaces together. The macrophage enveloping the particle is then delivered to lysosomes where the particle is ingested.

As used herein in relation to detection, diagnostic, therapeutic, and prophylactic methods, the term "canine influenza virus" is meant to refer to all canine influenza viruses, except where it clearly refers to a single strain of canine influenza virus. Examples of canine influenza viruses include, without limitation, the following: A/canine/New York/03, A/canine/New York/05, A/canine/Florida/03, A/canine/Florida/04, A/canine/Florida/43/04, A/canine/Florida/242/03, A/canine/Texas/04, A/canine/Texas/1/04, and A/canine/Iowa/13628/05.

The present invention also relates to a wide array of therapeutic and/or prophylatic agents and diagnostic procedures for, respectively, treating and detecting canine influenza virus disease in canine subjects.

For example, an effective amount of the proteins or polypeptides of the present invention can be administered alone or in combination with a pharmaceutically-acceptable carrier to canine subjects, as a vaccine, for preventing onset of disease resulting from infection by a canine influenza virus. Alternatively, it is possible to administer to canine subjects exposed to a canine influenza virus an effective amount of an antibody or binding portion thereof against these proteins or polypeptides as a passive immunization. Such antibodies or binding portions thereof are administered alone or in combination with a pharmaceutically-acceptable carrier to effect short term treatment of canine subjects who may have been recently exposed to a canine influenza virus.

Antibodies suitable for use in inducing passive immunity can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e., the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference in its entirety.

Mammalian lymphocytes are immunized by in vivo immunization of the animal (e.g., a mouse) with one of the proteins or polypeptides of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (see Milstein and Kohler, *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering one of the proteins or polypeptides of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbitol 150 mg/Kg IV. This and other procedures for raising polyclonal antibodies are disclosed in E. Harlow et. al., editors, *Antibodies: A Laboratory Manual* (1988), which is hereby incorporated by reference in its entirety.

In addition to utilizing whole antibodies, the processes of the present invention encompass use of binding portions of such antibodies. Such antibody fragments can be made by conventional procedures, such as proteolytic fragmentation procedures, as described in J. Goding, *Monoclonal Antibodies: Principles and Practice,* pp. 98-118 (N.Y. Academic press 1983), which is hereby incorporated by reference in its entirety.

The vaccines and passive immunization agents of this invention can be administered orally, parenterally, for example, subcutaneously, intravenously, intramuscularly, intraperitoneally, by intranasal installation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

Examples of suitable carriers for use in the vaccines of the present invention are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example antimicrobials, antioxidants, chelating agents, inert gases and the like. Preferred preservatives include formalin, thimerosal, neomycin, polymyxin B and amphotericin B.

As mentioned herein above, the isolated canine influenza virus according to the present invention can be incorporated into a vaccine as a live or inactivated virus. A general description of the preparation of veterinary vaccine compositions is found in "Handbuch der Schutzimpfungen in der Tiermedizin" (eds.: Mayr, A. et al., Verlag Paul Parey, Berlin und Hamburg, Germany, 1984) and "Vaccines for Veterinary Applications" (ed.: Peters, A. R. et al., Butterworth-Heinemann Ltd, 1993), which are hereby incorporated by reference in their entirety.

In one embodiment, the vaccine according to the invention containing the live canine influenza virus can be prepared and marketed in the form of a (frozen) suspension or in a lyophilized form. The vaccine can additionally contain a pharmaceutically acceptable carrier or diluent customary used for such compositions. Carriers include stabilizers, preservatives and buffers. Suitable stabilizers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

The vaccine of the present invention may further comprise one or more additional immunomodulatory components such as, e.g., an adjuvant or cytokine. The term "adjuvant" refers to a compound or mixture that enhances the immune response and/or promotes the proper rate of absorption following inoculation, and, as used herein, encompasses any uptake-facilitating agent. Non-limiting examples of adjuvants include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co-polymer (CytRx, Atlanta Ga.), QS-21 (Cambridge Biotech Inc., Cambridge Mass.), and SAF-M (Chiron, Emeryville Calif.), AMPHIGEN® adjuvant, saponin, Quil A or other saponin fraction, monophosphoryl lipid A, and Avridine lipid-amine adjuvant, and METASTIM®. Other suitable adjuvants can include, for example, surface active substances such as lysolecithin, pluronic polyols, polyanions, peptides, oil or hydrocarbon emulsions, keyhole limpet hemocyanins, dinitrophenol, and others. Specific non-limiting examples of oil-in-water emulsions useful in the vaccine of the invention include SEAM62 and SEAM ½, the components of which are known by those of ordinary skill in the art. Other immunomodulatory agents which may be included in the vaccine include, e.g., one or more interleukins, interferons, or other known cytokines. The vaccine may be stored in solution or, alternatively, in lyophilized form to be reconstituted with a sterile diluent solution prior to administration.

Other suitable examples compounds (e.g., adjuvants) that can be included in the vaccine of the present invention are ethylene maleic anhydrate (EMA) copolymer, latex emulsions of a copolymer of styrene with a mixture of acrylic acid and methacrylic acid, such as NEOCRYL A-640 (Avecia Neo Resius, Frankfort, Ind.), aluminum hydroxide, or the like, or a mixture thereof. The antibody response-inducing agent of the present invention can include a mixture of EMA and NEOCRYL (NEOCRYL is a registered trade name of Avecia BV, Sluisweg 12 P.O. Box 123 NL-5140 AC Waalwijk Netherlands), for water borne acrylic polymers and copolymers.

Other suitable agents, capable of enhancing a cellular immunity response, can be included with the vaccine of the present invention. Examples include biologics, such as an attenuated strain of *Mycobacterium bovis*, Bacille Calmette-Guerin (BCG) (Calbiochem, La Jolla, Calif.) or the like, and Th1-related cytokines, such as interleukin-12 (IL-12), interleukin-18 (IL-18), gamma interferon or the like, preferably IL-12; or substances that are oil-in-water emulsions, such as a paraffin oil-in- water emulsion like EMULSIGEN® SA (MVP Laboratories, Ralston, Nebr.), SP oil (a composition of squalane, Pluronic® L 121 and Tween® 80 (squalane is from VWR/Kodak Rochester, N.Y., and the Pluronic® L121 available from BASF, Mt. Olive, N.J.), SAF-1 (Syntex Adjuvant Formulation-1, a composition of the threonyl analog of muramyl dipetide, Tween 80, Pluronic® L121 and squalene, which is described by Byars, N. E. and Allison, A. C., *Vaccine* 5(3):223-228 (1987), which is hereby incorporated by reference in its entirety) or the like, preferably, EMULSIGEN® SA and more preferably, an oil-in-water emulsion. EMULSIGEN® is a registered trademark of Modern Veterinary Products, 5404 Miller Ave. Omaha, Nebr. 68127, U.S.A., for veterinary antigen adjuvants of an emulsified oil-in-water nature. The letters SA denotes a grade thereof. EMULSIGEN® SA, a paraffin emulsified oil adjuvant base, is milky-white when mixed with Tryptic Soy Broth (TSB) (20% final concentration), with a viscosity of 25-50 cps (Brookfield LV viscometer, spindle #18, at 30 rpm), and comprises at least 80% of oil phase droplets less than or equal to eight (8) microns. Pluronic® is a registered trademark of BASF Corporation for block copolymers of ethylene oxide and propylene oxide and the numeral L121 denotes a grade thereof.

The vaccine of the present invention may optionally be formulated for the sustained release of the antigen. Examples of such sustained release formulations include homogenate in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the homogenate may be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Pub. WO 95/28227, all of which are incorporated herein by reference. Liposomes may also be used to provide for the sustained release of the homogenate of the invention. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

In another embodiment the present invention provides a vaccine against disease conditions resulting from canine influenza virus infection including the isolated canine influenza virus of the present invention in an inactivated form. One advantage of an inactivated vaccine is the elevated levels of protective antibodies of long duration that can be obtained. The preparation of an inactivated canine influenza virus vaccine according to the present invention can be obtained by routine methods well known to the person skilled in the art. A vaccine containing the inactivated canine influenza virus can include, for example, one or more of the above-mentioned pharmaceutically acceptable carriers or diluents suited for this purpose. Inactivated vaccines can be administered parenterally, e.g., intramuscularly or subcutaneously, or by other well known methods, including those described herein. Suitable inactivating agents may be selected from the group consisting of formalin, beta-propiolactone (BPL), heat, binary ethylenimine (BEI), detergents and freeze/thaw with the preferred inactivating agents being BEI and BPL. The canine influenza virus can also be inactivated by conventional inactivation means. For example, chemical inactivation using chemical inactivating agents such as binary ethyleneimine, beta-propiolactone, formalin, merthiolate, gluteraldehyde, sodium dodecyl sulfate, or the like, or a mixture thereof. Inactivation can also be achieved using heat or psoralen in the presence of ultraviolet light.

The solid unit dosage forms can be of the conventional type. The solid form can be a capsule, such as an ordinary gelatin type containing the proteins or peptides of the present invention or the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The effective immunizing amount of the inactivated chosen strain or strains may be any amount sufficient to evoke a protective immune response. In one embodiment, the vaccine containing the live, attenuated canine influenza virus can be administered in a dose of between about $10^3$ to $10^5$ $TCID_{50}$. In another embodiment, the vaccine containing inactivated canine influenza virus can be administered in a dose of between about 300-1200 hemagglutinin ("HA") units, and more particularly between about 500-800 HA units.

The canine influenza virus vaccine of the present invention can also be administered in combination with one or more other vaccines used to treat or protect against other canine pathogens/diseases. Examples of such other vaccines can include, for example, vaccines against (i) canine viral pathogens such as canine parvovirus (CPV), canine distemper virus (CDV), canine adenovirus (CAV), canine parainfluenza virus (CPI), canine coronavirus (CCV), and the rabies virus; (ii) canine bacterial pathogens such as *Borrelia burgdoferi, Bordetella bronchiseptica, Leptospira* spp., and *Ehrlichia canis*; and (iii) canine protozoan pathogens such as *Leishmania* and *Giardia*.

The isolated nucleic acid molecules, proteins, or polypeptides of the present invention or the antibodies or binding portions raised against the proteins or polynucleotides of this invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

The present invention also relates to a method of vaccinating canine subjects against onset of disease caused by infection of a canine influenza virus. This method involves administering to a canine subject an effective amount of the isolated nucleic acid molecule of the present invention. Suitable techniques for such gene therapy techniques are well known and are described in U.S. Pat. Nos. 5,328,470 and 6,339,068, the entire disclosures of which are hereby incorporated by reference.

For use as aerosols, the proteins or polypeptides of the present invention or the antibodies or binding portions thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In yet another aspect of the present invention, the proteins or polypeptides of the present invention can be used as antigens in diagnostic assays for the detection of a canine influenza virus in body fluids. Alternatively, the detection of a canine influenza virus can be achieved with a diagnostic assay employing antibodies or binding portions thereof raised by such antigens. Such techniques permit detection of a canine influenza virus in a sample of the following tissue or body fluids: mucos, saliva, lungs, blood, spinal fluid, sputum, pleural fluids, urine, bronchial alveolor lavage, lymph nodes, bone marrow, or other biopsied materials.

In one embodiment, the assay system has a sandwich or competitive format. Examples of suitable assays include an enzyme-linked immunosorbent assay (ELISA), a radioimmunoassay, a gel diffusion precipitan reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequences of the isolated nucleic acid molecules of the present invention may be used as a probe in nucleic acid hybridization assays for the detection of canine influenza virus in various body fluids. The nucleotide sequences of the present invention may be used in any nucleic acid hybridization assay system known in the art, including, but not limited to, Southern blots (see Southern, *J. Mol. Biol.* 98: 503-517 (1975), which is hereby incorporated by reference in its entirety, which discloses hybridization in 2×SSC (i.e., 0.15M NaCl, 0.015 sodium citrate), 40% formamide at 40 degrees Celsius); Northern blots (see Thomas et al., *Proc. Nat'l Acad. Sci. USA* 77:5201-05 (1980), which is hereby incorporated by reference in its entirety); and Colony blots (see Grunstein et al. *Proc. Nat'l Acad. Sci. USA* 72:3961-65 (1975), which are hereby incorporated by reference in their entirety). Alternatively, the isolated DNA molecules of the present invention can be used in a gene amplification detection procedure (e.g., a polymerase chain reaction). See H. A. Erlich et. al., "Recent Advances in the Polymerase Chain Reaction," *Science* 252:1643-51 (1991), which is hereby incorporated by reference in its entirety.

EXAMPLES

The Example set forth below is for illustrative purposes only and is not intended to limit, in any way, the scope of the present invention.

Example 1

Isolation of Canine Influenza Virus
A/Canine/NY/115809/05

Sample that was received at the Animal Health Diagnostic Center was a pharyngeal swab from a 10 year old golden retriever. The extract from the swab was divided into two aliquots. One was part of the sample was tested for influenza virus nucleic acid by the polymerase chain reaction test targeting the matrix gene. The other part of the sample was placed at −70° C. until PCR results were available. Upon learning of a positive test by PCR, the frozen sample was thawed and used to inoculate MDCK cells and embryonated eggs. The MDCK cells were cultured with trypsin in the growth medium to enhance the growth of influenza. After several days in culture, abnormal cell morphology was detected that was not present in the control cultures. After 6 days, the cells were frozen. A thawed extract was used to inoculate new MDCK cells. After 6 days, the cell monolayer was destroyed. The eggs were incubated for 3 days and then the allantoic fluids harvested. Presence of an "A" type influenza was determined by an antigen-capture ELISA commercial test kit. Both the cell culture system and the egg system were able to grow a virus that was determined to be canine influenza by nucleotide sequencing.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated canine influenza virus comprising a hemagglutinin gene having the nucleotide sequence of SEQ ID NO:1.

2. The isolated canine influenza virus according to claim 1, wherein said hemagglutinin gene encodes a protein or polypeptide having the amino acid sequence of SEQ ID NO:2.

3. The isolated canine influenza virus according to claim 1, wherein said isolated canine influenza virus is in a live form or live-attenuated form.

4. The isolated canine influenza virus according to claim 1, wherein said isolated canine influenza virus is in an inactive form.

5. The isolated canine influenza virus according to claim 1, wherein said isolated canine influenza virus is in a recombinant form.

6. An isolated nucleic acid molecule encoding a hemagglutinin of a canine influenza virus, wherein said hemagglutinin comprises a protein or polypeptide having the amino acid sequence of SEQ ID NO:2.

7. The isolated nucleic acid molecule according to claim 6, wherein said isolated nucleic acid molecule comprises a nucleotide sequence of SEQ ID NO:1.

8. The isolated nucleic acid molecule according to claim 6, wherein said isolated nucleic acid molecule comprises the nucleotide coding sequence corresponding to bases 16 through 1710 of SEQ ID NO:1.

9. The isolated nucleic acid molecule according to claim 6, wherein said canine influenza virus is comprises canine influenza virus strain A/canine/NY/OS.

10. An isolated canine influenza virus hemagglutinin protein or polypeptide, wherein said protein or polypeptide comprises the amino acid sequence of SEQ ID NO:2.

11. The isolated protein or polypeptide according to claim 10, wherein said protein or polypeptide is encoded by a nucleic acid molecule having the nucleotide sequence of SEQ ID NO:1.

12. The isolated protein or polypeptide according to claim 10, wherein said protein or polypeptide is encoded by the nucleic acid molecule comprising nucleotide sequence corresponding to bases 16 through 1710 of SEQ ID NO:1.

13. The isolated protein or polypeptide according to claim 10, wherein said protein or polypeptide is recombinant.

14. The isolated protein or polypeptide according to claim 10, wherein said protein or polypeptide is purified.

15. A recombinant expression system comprising an expression vector into which is inserted a heterologous nucleic acid molecule, wherein said heterologous nucleic acid molecule comprises the isolated nucleic acid molecule according to claim 6.

16. An isolated host cell incorporating a heterologous nucleic acid molecule, wherein said heterologous nucleic acid molecule comprises the isolated nucleic acid molecule according to claim 6.

17. The isolated host cell according to claim 16, wherein said heterologous isolated nucleic acid molecule is inserted in a recombinant expression system comprising an expression vector.

* * * * *

SEQUENCE LISTING

<160> NUMBER OF SEQ ID NOS: 2

<210> SEQ ID NO 1

<211> LENGTH: 1728
<212> TYPE: DNA
<213> ORGANISM: Canis familiaris

<400> SEQUENCE: 1

```
atatttctgt caatcatgaa gacaaccatt attttaatac tactgaccca ttgggcctac      60
agtcaaaacc caatcagtgg caataacaca gccacactgt gtctgggaca ccatgcagta     120
gcaaatggaa cattggtaaa aacaatgagt gatgatcaaa ttgaggtaac aaatgctaca     180
gaattagttc agagcatttc aatggggaaa atatgcaaca aatcatatag aattctagat     240
ggaagaaatt gcacattaat agatgcaatg ctaggagacc cccactgtga cgcctttcag     300
tatgagagtt gggacctctt tatagaaaga agcaacgctt tcagcaattg ctacccatat     360
gacatccctg actatacatc gctccgatcc attgtagcat cctcaggagc agtggaattc     420
acagcagagg gattcacatg gacaggtgtc actcaaaacg gaagaagtgg agcctgcaaa     480
agggatcag ccgatagttt ctttagccga ctgaattggc taacaaaatc tggaagctct     540
taccccacat tgaatgtgac aatgcctaac aataaaaatt tcgacaagct atacatctgg     600
gggattcatc acccgagctc aaatcaagag cagacaaaat tgtacatcca gaatcagga      660
cgagtaacag tctcaacaaa agaagtcaa caaacaataa tccctaacat cggatctaga     720
ccgttggtca gaggtcaatc aggcaggata agcatatact ggaccattgt aaaacctgga     780
gatatcctaa tgataaacag taatggcaac ttagttgcac cgcgggata ttttaaattg      840
aacacaggga aaagctctgt aatgagatcc gatgtaccca tagacatttg tgtgtctgaa     900
tgtattacac caaatggaag catctccaac gacaagccat tccaaaatgt gaacaaagtt     960
acatatggaa aatgccccaa gtatatcagg caaaacactt taaagctggc cactgggatg    1020
aggaatgtac cagaaaagca aaccagagga atctttggag caatagcggg attcatcgaa    1080
aacggctggg aaggaatggt tgatgggtgg tatgggttcc gatatcaaaa ctctgaagga    1140
acagggcaag ctgcagatct aaagagcact caagcagcca tcgaccagat taatggaaag    1200
ttaaacagag tgattgaaag aaccaatgag aaattccatc aaatagagaa ggaattctca    1260
gaagtagaag gaagaattca ggacttggag aaatatgtag aagacaccaa aatagaccta    1320
tggtcctaca atgcagaatt gctggtggct ctagaaaatc aacatacaat tgacttaaca    1380
gatgcagaaa tgaataaatt atttgagaag actagacgcc agttaagaga aaacgcagaa    1440
gacatgggag tggatgtttt caagatttac cacaaatgtg ataatgcatg cattgaatca    1500
ataagaactg aacatatga ccattacata tacagagatg aagcattaaa caaccgattt    1560
cagatcaaag gtgtagagtt gaaatcaggc tacaaagatt ggatactgtg gatttcattc    1620
gccatatcat gcttcttaat ttgcgttgtt ctattgggtt tcattatgtg ggcttgccaa    1680
aaaggcaaca tcagatgcaa catttgcatt tgagtaaact gatagtta              1728
```

<210> SEQ ID NO 2
<211> LENGTH: 565
<212> TYPE: PRT
<213> ORGANISM: Canis familiaris

<400> SEQUENCE: 2

```
Met Lys Thr Thr Ile Ile Leu Ile Leu Leu Thr His Trp Ala Tyr Ser
 1               5                  10                  15

Gln Asn Pro Ile Ser Gly Asn Asn Thr Ala Thr Leu Cys Leu Gly His
                20                  25                  30

His Ala Val Ala Asn Gly Thr Leu Val Lys Thr Met Ser Asp Asp Gln
```

-continued

```
            35                  40                  45
Ile Glu Val Thr Asn Ala Thr Glu Leu Val Gln Ser Ile Ser Met Gly
 50                  55                  60

Lys Ile Cys Asn Lys Ser Tyr Arg Ile Leu Asp Gly Arg Asn Cys Thr
 65                  70                  75                  80

Leu Ile Asp Ala Met Leu Gly Asp Pro His Cys Asp Ala Phe Gln Tyr
                     85                  90                  95

Glu Ser Trp Asp Leu Phe Ile Glu Arg Ser Asn Ala Phe Ser Asn Cys
                    100                 105                 110

Tyr Pro Tyr Asp Ile Pro Asp Tyr Thr Ser Leu Arg Ser Ile Val Ala
                    115                 120                 125

Ser Ser Gly Ala Val Glu Phe Thr Ala Glu Gly Phe Thr Trp Thr Gly
        130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                    165                 170                 175

Pro Thr Leu Asn Val Thr Met Pro Asn Asn Lys Asn Phe Asp Lys Leu
                180                 185                 190

Tyr Ile Trp Gly Ile His His Pro Ser Ser Asn Gln Glu Gln Thr Lys
                195                 200                 205

Leu Tyr Ile Gln Glu Ser Gly Arg Val Thr Val Ser Thr Lys Arg Ser
        210                 215                 220

Gln Gln Thr Ile Ile Pro Asn Ile Gly Ser Arg Pro Leu Val Arg Gly
225                 230                 235                 240

Gln Ser Gly Arg Ile Ser Ile Tyr Trp Thr Ile Val Lys Pro Gly Asp
                    245                 250                 255

Ile Leu Met Ile Asn Ser Asn Gly Asn Leu Val Ala Pro Arg Gly Tyr
                260                 265                 270

Phe Lys Leu Asn Thr Gly Lys Ser Ser Val Met Arg Ser Asp Val Pro
                275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                    325                 330                 335

Asn Val Pro Glu Lys Gln Thr Arg Gly Ile Phe Gly Ala Ile Ala Gly
                340                 345                 350

Phe Ile Glu Asn Gly Trp Glu Gly Met Val Asp Gly Trp Tyr Gly Phe
                355                 360                 365

Arg Tyr Gln Asn Ser Glu Gly Thr Gly Gln Ala Ala Asp Leu Lys Ser
        370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                    405                 410                 415

Val Glu Gly Arg Ile Gln Asp Leu Glu Lys Tyr Val Glu Asp Thr Lys
                420                 425                 430

Ile Asp Leu Trp Ser Tyr Asn Ala Glu Leu Leu Val Ala Leu Glu Asn
                435                 440                 445

Gln His Thr Ile Asp Leu Thr Asp Ala Glu Met Asn Lys Leu Phe Glu
        450                 455                 460
```

```
Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Arg Asp Glu Ala Leu Asn
                500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Ile Cys Val
        530                 535                 540

Val Leu Leu Gly Phe Ile Met Trp Ala Cys Gln Lys Gly Asn Ile Arg
545                 550                 555                 560

Cys Asn Ile Cys Ile
            565
```